United States Patent
Litt et al.

(10) Patent No.: US 6,658,287 B1
(45) Date of Patent: Dec. 2, 2003

(54) METHOD AND APPARATUS FOR PREDICTING THE ONSET OF SEIZURES BASED ON FEATURES DERIVED FROM SIGNALS INDICATIVE OF BRAIN ACTIVITY

(75) Inventors: Brian Litt, Merion Station, PA (US); George Vachtsevanos, Marietta, GA (US); Javier Echauz, Dunwoody, GA (US); Rosana Esteller, Marietta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 0 days.

(21) Appl. No.: 09/762,455
(22) PCT Filed: Aug. 24, 1999
(86) PCT No.: PCT/US99/19387
§ 371 (c)(1),
(2), (4) Date: May 18, 2001
(87) PCT Pub. No.: WO00/10455
PCT Pub. Date: Mar. 2, 2000

Related U.S. Application Data
(60) Provisional application No. 60/129,420, filed on Apr. 15, 1999, and provisional application No. 60/097,580, filed on Aug. 24, 1998.

(51) Int. Cl.$^7$ ................................................. A61B 5/04
(52) U.S. Cl. ....................................................... 600/544
(58) Field of Search ................................ 600/544, 545, 600/546, 300; 607/45, 62

(56) References Cited
U.S. PATENT DOCUMENTS

| | | |
|---|---|---|
| 3,837,331 A | 9/1974 | Ross |
| 3,850,161 A | 11/1974 | Liss |
| 3,863,625 A | 2/1975 | Viglione et al. |
| 3,967,616 A | 7/1976 | Ross |

(List continued on next page.)

FOREIGN PATENT DOCUMENTS

| | | |
|---|---|---|
| WO | WO97/26823 | 7/1997 |
| WO | WO 00/10455 | 3/2000 |

OTHER PUBLICATIONS

Osorio, I. et al., "Real–Time Automated Detection and Quantitative Analysis of Seizures and Short–Term Prediction of Clinical Onset", Epliepsia, vol. 39, No. 6, Jun. 1998, pp. 615–627.

"Automated Seizure Prediction Paradigm" *Epilepsia* 39:56 (1998).

(List continued on next page.)

*Primary Examiner*—Eric F. Winakur
*Assistant Examiner*—Brian Szmal
(74) *Attorney, Agent, or Firm*—Needle & Rosenberg, P.C.

(57) ABSTRACT

This invention is a method, and system for predicting the onset of a seizure prior to electrograph onset in an individual. During an "off-line" mode, signals representing brain activity of an individual (either stored or real time) are collected, and features are extracted from those signals. A subset of features, which comprise a feature vector, are selected by a predetermined process to most efficiently predict (and detect) a seizure in that individual. An intelligent prediction subsystem is also trained "off-line" based on the feature vector derived from those signals. During "on-line" operation, features are continuously extracted from real time brain activity signals to form a feacture vector, and the feature vector is continuously analyzed with the intelligent prediction subsystem to predict seizure onset in a patient. The system, and method are preferably implemented in an implanted device (102) that is capable of warning externally an individual of the probability of a seizure, and/or automatically taking preventative actions to abort the seizure. In addition, methods are provided for applying intervention measures to an animal to abort or modulat a seizure by adjusting the modality of an intervention measure; and/or parameters of an intervention measure based upon a probability measure indicative of a likelihood of seizure occurrence; and/or a predicted time to seizure onset.

39 Claims, 20 Drawing Sheets

U.S. PATENT DOCUMENTS

| | | | |
|---|---|---|---|
| 3,993,046 | A | 11/1976 | Fernandez et al. |
| 4,566,464 | A | 1/1986 | Piccone et al. |
| 4,702,254 | A | 10/1987 | Zabara |
| 4,867,164 | A | 9/1989 | Zabara |
| 5,025,807 | A | 6/1991 | Zabara |
| 5,304,206 | A | 4/1994 | Baker, Jr. et al. |
| 5,311,876 | A | 5/1994 | Olsen et al. |
| 5,713,923 | A | 2/1998 | Ward et al. |
| 5,720,294 | A | 2/1998 | Skinner |
| 5,743,860 | A | 4/1998 | Hively et al. |
| 5,857,978 | A | 1/1999 | Hively et al. |
| 5,928,272 | A | 7/1999 | Adkins et al. |
| 5,978,702 | A | 11/1999 | Ward et al. |
| 5,995,868 | A | 11/1999 | Dorfmeister et al. |
| 6,016,449 | A | 1/2000 | Fischell et al. |
| 6,018,682 | A | 1/2000 | Rise |
| 6,061,593 | A | 5/2000 | Fischell et al. |

OTHER PUBLICATIONS

Cover "The Best Two Independent Measurements are Not the Two Best" *IEEE Transactions on System, Man, and Cybernetics* (Jan. 1974).

Echauz et al. "Eliptic and Radial Wavelet Neural Networks" in *Proc. Second World Automation Congress, Montpellier, France, May 27–30, 1996* 5:173–179 (1996).

Echauz et al. "Neuro–Fuzzy Approaches to decision Making: A Comparative Study with an Application to check Authorization"0 *J. of Intelligent and Fuzzy Sys.* 6:259–278 (1998).

Elger et al. "Seizure Prediction by Nonlinear Time Series Analysis of Brain Electrical Activity," *European J. of Neuroscience* 10:786–789 (1998).

Grassberger et al. "Characterization of Strange Attractors" *Physical Rev. Letters* 50 (5) :346–349.

Iasemidis et al. "Chaos Theory and Epilepsy" *The Neuroscienst* 2 (2) :118–126 (Mar. 1996).

Iasemidis et al. "Spatiotemporal Elvolution of Dynamical Measures Precedes Onset of Mesial Temporal Lobe Seizures" *Epilepsia*, 35 (8) :133 (1994).

Webber et al. "Auto EEG Spike Detection: What Should the Computer Imitate?" *Electroencephalograhy and Clinical Neurophysiology* 84:364–373 (1993).-

AP  EO  AD  CO

OBSERVATION WINDOW — PREDICTED HORIZON — SEIZURE

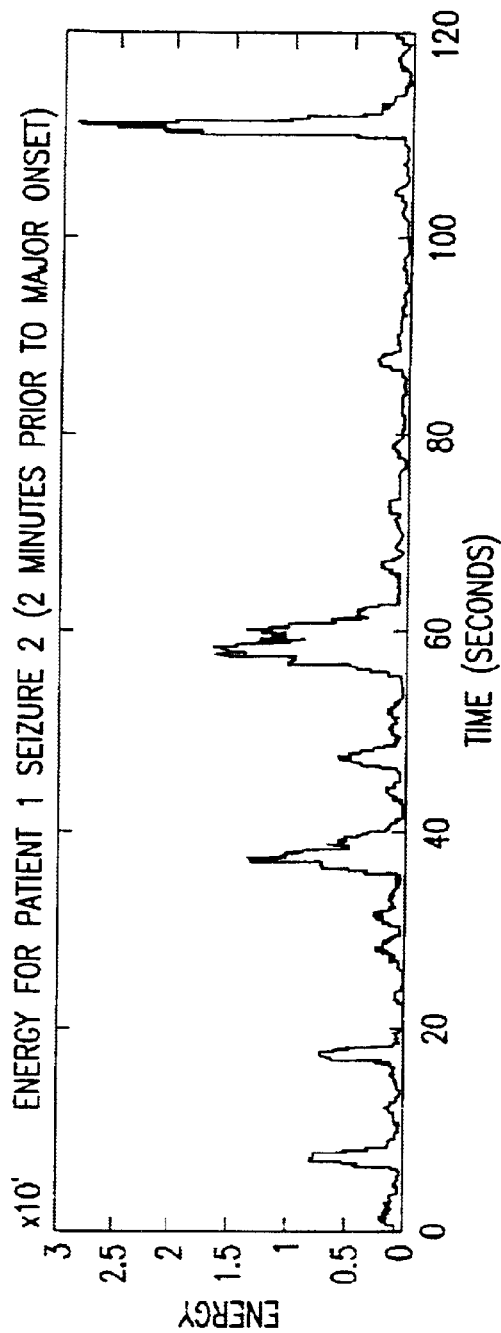
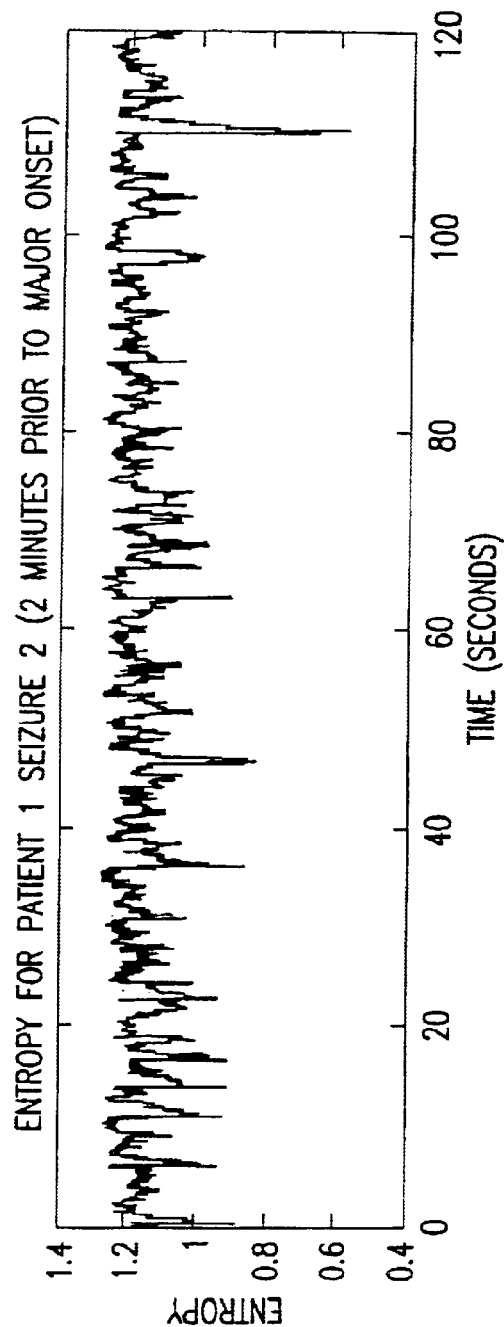

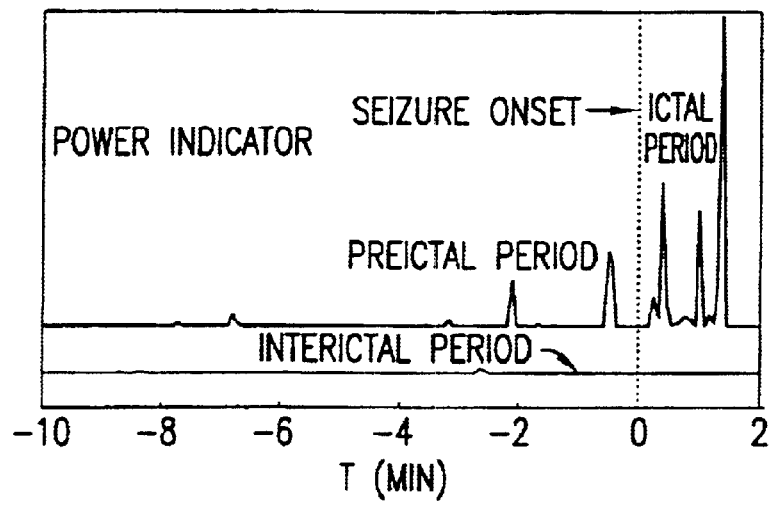
FIG. 17
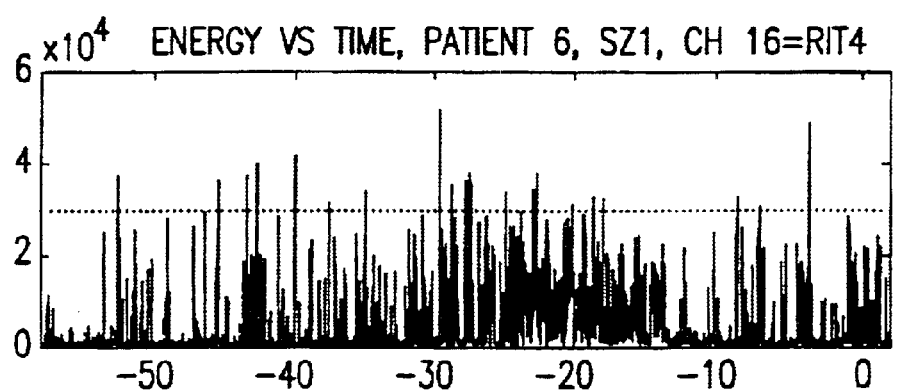
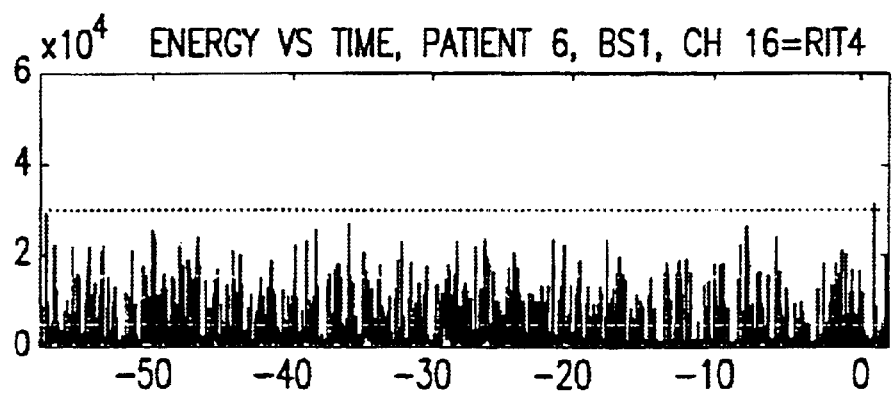
FIG. 18

U S 6,658,287 B1

METHOD AND APPARATUS FOR PREDICTING THE ONSET OF SEIZURES BASED ON FEATURES DERIVED FROM SIGNALS INDICATIVE OF BRAIN ACTIVITY

This application claims priority to U.S. Provisional Application No. 60/097,580 filed Aug. 24, 1998 and U.S. Provisional Application No. 60/129,420 filed Apr. 15, 1999.

FIELD OF THE INVENTION

The present invention is directed to predicting the onset of epileptic seizures, and more specifically to a method and apparatus for automatically interpreting information representing the activity of the brain so as to predict the onset of a seizure in order to alert a patient of the possibility of an impending seizure and/or to take preventative actions to avert a seizure.

BACKGROUND OF THE INVENTION

Epilepsy affects approximately 1% of the population in the United States and approximately 2% of the population worldwide. Of those affected by the disease, approximately one-third have seizures that cannot be controlled by medication or cured by surgery. Epilepsy surgery requires locating the region of the brain where seizure onset occurs and the pathways through which the seizures spread, a process that is not completely accurate and reliable. Moreover, epilepsy surgery is accompanied by the inherent risk of neurologic injury, disfigurement and other complications. Some individuals have epileptic seizures that cannot be controlled by standard medication, are inoperable because seizure onset is not localized, or originate from vital areas of the brain which cannot be surgically removed. These individuals may resort to high doses of intoxicating medications and/or other experimental therapies.

Several prior art algorithms for seizure prediction and/or detection are known. See, for example, U.S. Pat. No. 5,857,978, to Hively et al., entitled "Epileptic Seizure Prediction by Nonlinear Methods," U.S. Pat. No. 3,863,625, to Viglione et al., entitled "Epileptic Seizure Warning System," U.S. Pat. No. 4,566,464, entitled "Implantable Epilepsy Monitor Apparatus."

It is desirable to provide a method and apparatus for predicting seizures with such accuracy that the activity of the brain can be monitored by an implantable device to warn a patient of the likelihood of an impending seizure, and/or to take preventative actions through application of intervention measures to abort or modulate the seizure prior to clinical onset.

SUMMARY OF THE INVENTION

Briefly, the present invention is directed to a method and apparatus for predicting the onset of a seizure in an individual. Whereas prior art systems and algorithms determine that a seizure is occurring after detection of its actual electrical onset, which may or may not occur before detectable clinical manifestations of a seizure, the present invention is directed to a method and apparatus for predicting that a seizure is going to occur sometime well in advance of any detectable electrical onset or clinical onset of seizure activity. The prediction achieved according to the present invention is well in advance of any electrical onset of seizures, or clinical onset, and before there are visually obvious changes in EEG patterns.

The method and apparatus according to the present invention operate by monitoring signals representing the activity of the brain, extracting features from the signals and deriving a feature vector representing a combination of those features that are determined (during "off-line" analysis of a particular individual and/or other knowledge of seizure prediction across a number of individuals) to be predictive of seizure onset, and analyzing the feature vector with a trainable algorithm implemented by, for example, a wavelet neural network, to predict seizure onset. Features are extracted on both an instantaneous basis and a historical basis. Features are collected and analyzed in different time frames, such as over days, hours, minutes, and seconds.

Preferably, the system is implemented in an implantable device that an individual or physician can interface with in much the same manner as an implantable pacemaker or defibrillator. Interface to the implantable device is by way of a body-wearable or attachable patient access unit that includes a display (such as a liquid crystal display), an audible or visible alert, a vibration alert, and a user interface (such as a button keypad). The output of the implantable device may comprise a signal(s) indicating a probability of seizure occurrence within one or more specified periods of time in parallel. The patient may program the system via the patient access unit to generate certain levels of alerts based on programmable probability thresholds. Access may also take place via connection to a local or physician's office personal computer and to a central facility via the Internet. Programming can be done by the patients with their personal unit, or the physician may choose to completely control this process via periodic checks with an office unit, the patient's home PC or via the Internet, portable cellular, infra-red, microwave or other communication device.

In addition, the system may be programmed to automatically trigger preventative actions, such as the application of an electrical shock, the delivery of one or more drugs or the activation of a pacing algorithm which can be employed to abort the seizure or mitigate the severity of a seizure. Outputs from the device may be used to train the patient in a biofeedback scheme to learn to abort seizures themselves.

A distinguishing theme of the present invention is that the most accurate seizure predictor is one based on the synergy of multiple features or a single feature artificially customized from raw data, as opposed to prior art techniques that involve reliance on a single conventional feature. Another important aspect of the invention is the generation as output of one or more probability measures, each associated with a different prediction horizon, that represent the likelihood a seizure will occur during the corresponding prediction horizon.

Another aspect of the invention a method for applying intervention measures to an animal to abort or modulate a seizure comprising the step of adjusting the modality of an intervention measure and/or parameters of an intervention measure based upon a probability measure indicative of a likelihood of seizure occurrence and/or a predicted time to seizure onset.

The above and other objects and advantages of the present invention will become more readily apparent when reference is made to the following description taken in conjunction with the accompanying drawings.

BRIEF DESCRIPTION OF THE DRAWINGS

FIGS. 13–16 are timing diagrams for multiple features in time, frequency and chaotic domains, which show a synergy for seizure prediction.

FIG. 17 is a timing diagram of a power feature prior to and during a seizure, and illustrating the enhanced distinctive burst characteristics leading up to an ictal event.

FIG. 18 illustrates timing diagrams for energy at different time intervals with respect to seizure activity, and indicates the enhanced fluctuation in energy prior to the seizure in contrast times well removed from seizure activity.

DETAILED DESCRIPTION OF THE INVENTION

The present invention is directed to a system (i.e., method and apparatus) for predicting the onset of a seizure in an individual so that the individual or attending medical personnel can be warned of an impending seizure in order to prepare for it and/or take preventative actions to stop the seizure or substantially mitigate it. Furthermore, the present invention is directed to a fully automatic and interactive system that can be implanted in and/or worn by a patient to alert a patient of the possibility of an impending seizure so that appropriate action can be taken. This action may be undertaken either by the patient or a caregiver etc., or by automatically by the system itself.

The terms "individual" and "patient" used herein are meant to include animals in general, and particularly humans. The term "animal" is meant to include humans and non-human animals and the present invention may have utility in clinical and experimental research on non-human animals.

Figure 1:
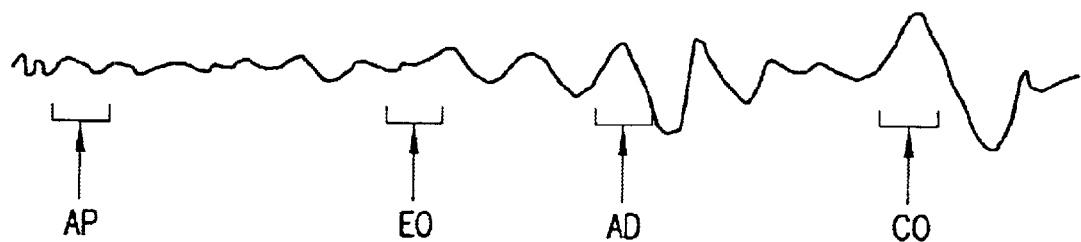
FIG. 1 is a stylized timing diagram of an electroencephalographic signal illustrating the distinction between seizure prediction and seizure detection according to the present invention.

FIG. 1 illustrates a signal from a single channel of an intracranial EEG and demonstrates the relationship between several important time periods (or events) with respect to the "prediction" of a seizure as opposed to the "detection" of a seizure, according to the present invention.

Timing Definitions

EO=Electrographic Onset of seizure. The beginning of seizure as marked by the current "gold standard" of expert visual analysis of EEG. EO can be further divided into EEC (earliest electrographic change), the earliest change in the EEG which could signify a seizure) and UEO (unequivocal electrographic onset), the point at which an electrographic seizure is absolutely clear to an expert electroencephalographer.

AD=Automated Detection of EO. The time when prior art algorithms first declare a seizure, normally after EO due to computational requirements, usage of inappropriate features, or lack of effective features.

CO=Clinical Onset. The time when a clinical seizure is first noticeable to an outside observer who is watching the patient from whom the EEG is recorded. CO can be further divided into ECC (earliest clinical change) that could signal a seizure onset and the UCO (unequivocal clinical onset).

AP=Automated Prediction of EO. The time at which an automated algorithm (such as the one according to the present invention) first predicts seizure onset. This will ordinarily be well in advance of any visible changes in the EEG or changes in the patient's behavior, and importantly, prior to EO.

PTOT=Prediction-To-Onset Time=EO minus AP

As is well known in the art, the events EO and CO are known to occur within some approximate period of time, and typically are not exactly localizable in time.

In accordance with the present invention, and as used hereinafter, seizure prediction means the declaration that a seizure is going to occur sometime well in advance of any detectable electrical (EO) or clinical onset (CO) of seizure activity. This is shown in FIG. 1 as the event AP. At EO, AD and CO, the actual seizure has already begun, though its clinical expression might not be easily apparent if the appropriate central nervous system function is not being tested at the time of electrical onset (e.g. the function corresponding to brain in the ictal onset zone). This is to be distinguished from all known prior art algorithms where brain activity is monitored to determine that a seizure is going to occur after detection of its actual electrical onset, which may or may not occur in advance of detectable clinical manifestations of a seizure. Therefore these known algorithms actually function only as seizure "detectors", and do not predict that a seizure is likely to occur. This is also distinguished from prior art prediction algorithms in that there is no exact time of AP. The present invention, on the other hand, involves generating a probability of prediction continuously in different time frames and the threshold declaration of AP is selectable/adjustable by the patient, care taker, physician, insurance company, etc.

Figure 2:
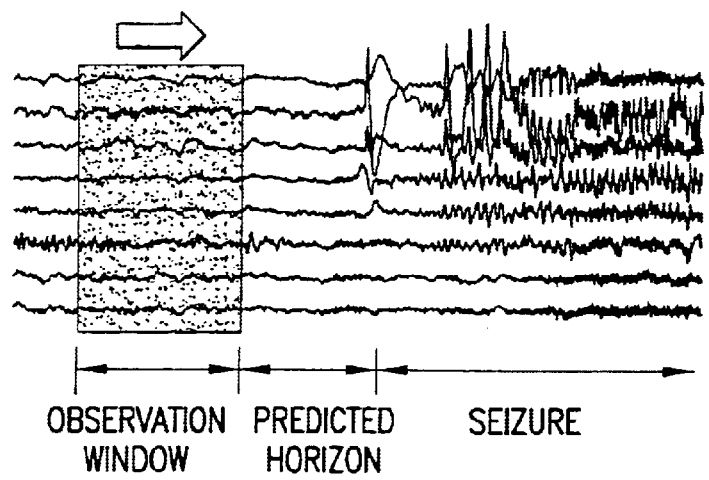
FIG. 2 is a timing diagram showing brain activity signals prior to and at the onset of a seizure.

With reference to FIG. 2, in accordance with the present invention, brain activity signals are continuously monitored in order to detect activity that is predictive of a seizure. The shaded block shown in FIG. 2 is a sliding observation window during which time processing of the brain activity signal is continuous. The period of time from the right edge of the observation window to the last instant when a seizure is pharmacologically or electrically preventable is called the prediction horizon. Beyond the prediction horizon, it is no longer possible to significantly deter the onset of the seizure with preventative measures heretofore known, though it may be possible to reduce or mitigate the full clinical expression of a seizure after this time. The pre-ictal time frame for seizure prediction may begin as much as 2–3 hours or more prior to seizure onset.

According to the present invention, a large set of independent, instantaneous and historical features are extracted from the intracranial EEG, real-time brain activity data and/or other physiologic data. Once extracted, the features are processed by a prediction algorithm or intelligent prediction subsystem, such as a wavelet neural network. The intelligent prediction subsystem looks for synergistic properties of these features which together predict seizure onset, though each of the features taken individually may not yield this same predictive information. The feature set is systematically pared down for each individual patient (during "off-line" analysis) to a subset of core parameters which yield maximal predictive value, minimal redundancy and minimal computational requirements. This process of adaptive training will take place periodically throughout the life of the device, and the feature set may be augmented by new or artificially synthesized features during this process. This feature set is represented in vector form, and called a feature vector. The feature vector is continuously derived from the raw data.

The feature vector is continuously analyzed by the intelligent prediction subsystem as raw data are input into the system. The system outputs a probability that a seizure will occur, or if the circumstances so indicate, that a seizure is occurring (i.e., seizure detection). This process is one in which the probability output by the system is dynamically updated. At one instant, it may appear the probability of a seizure as high, while at subsequent periods of time, the probability may be determined to be lower. This allows the system to learn the dynamics of seizure prediction (and detection) for a particular patient, and more accurately determine when a seizure is likely to occur.

THE SYSTEM

Figure 3:
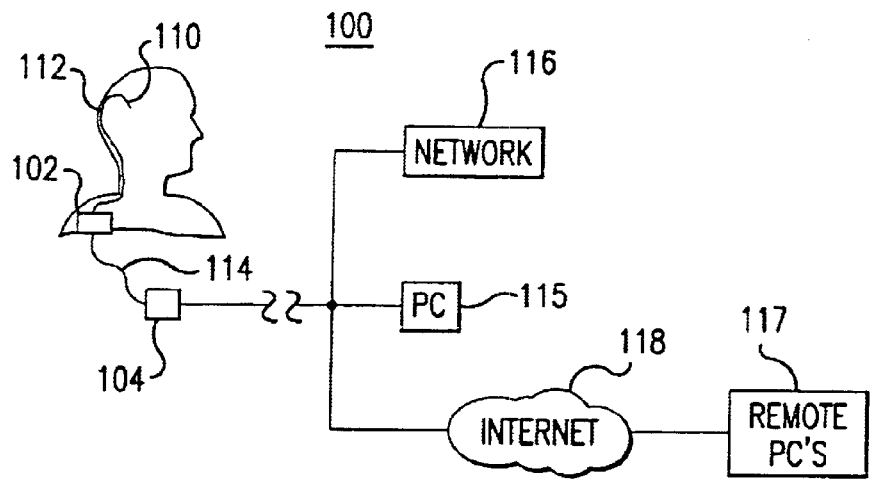
FIG. 3 is a general block diagram of a system for predicting the onset of a seizure according to the present invention.

FIG. 3 illustrates an example of the general architecture of a seizure prediction and control system according to the present invention. An implantable processing device (also referred to as the implanted unit) 102 and an external wearable processor device 104 (also referred to as the portable unit) are shown. The implanted unit 102 is contained within a bio-compatible housing/enclosure that is implanted in a patient, such as under a patient's clavicle. The components of the portable unit 104 are contained within a housing that is worn on the patient, similar to a cellular telephone, pager, etc.

The electrodes 110 detect signals representative of the activity of the brain. For example, the electrodes 110 may be intracranial electrodes (i.e., depth wires, subdural strips, peg electrodes, etc.); intra-, extra- or trans-vascular electrodes; epidural or bone screw electrodes; scalp electrodes; or other electrodes, such as sphenoidal electrodes, or foramen ovale electrodes. The electrodes 110 may detect electroencephalogram (EEG) signals, the DC level of EEG signals, electrochemical changes (such as glutamate levels) or magnetoencephalogram signals. Leads 112 are tunneled under the skin to connect the electrodes 110 to the circuitry in the implanted unit 102. Other physiologic sensors such as those which monitor heart rate variability, vagus nerve impulses, brain blood flow, serum chemistry (for example, epinephrine levels), may also be useful to obtain physiologic signals according to the present invention.

The portable unit 104 may be some form of a device which may combine features of wearable computers, cellular phones, and personal digital assistants. Alternatively, the system can be configured so that the portable unit 104 is not worn but rather periodically coupled to the patient for bi-directional data/program transfer. For example, the portable unit 104 can be a type that is placed in a cradle for uploaded data obtained from the implanted unit.

The link 114 between the implanted unit 102 and the portable unit 104 is a electrical conductor link, optical link, magnetic link, radio frequency link, sonographic link or other types of wireless links. Depending on the type of link the implanted unit 102 and the portable unit 104 has the appropriate hardware to achieve communication with each other.

The portable unit 104 is also connectable (using standard cable, docketing station or cradle configurations, or other types of interfaces known in the art) to a personal computer (PC) 115, a network 116, or to remotely located PCs 117 via the Internet 118. For example, data obtained from the implanted unit 110 can be stored and periodically up-loaded though the interface between the implantable unit 102 and the portable unit 104 during quiet periods far removed from seizures. In this way, the implanted unit 102 can have a relatively smaller buffer size. The portable unit 104 may include a hard drive storage device having a storage capacity in the gigabyte range. Similarly, information can be downloaded to the portable unit 104 and/or the implanted unit 102 from the PC 115, network 116, or remote PCs 117 to adjust various parameters as will become more apparent hereinafter. The portable unit 104 also serves as a user interface for the patient or doctor to set alarm thresholds and other options, and as a data communications interface as explained above. Moreover, all of the functions that could be performed directly on the portable unit 104 can also be performed remotely from the PC 115 or remote PCs 117.

Figure 4:
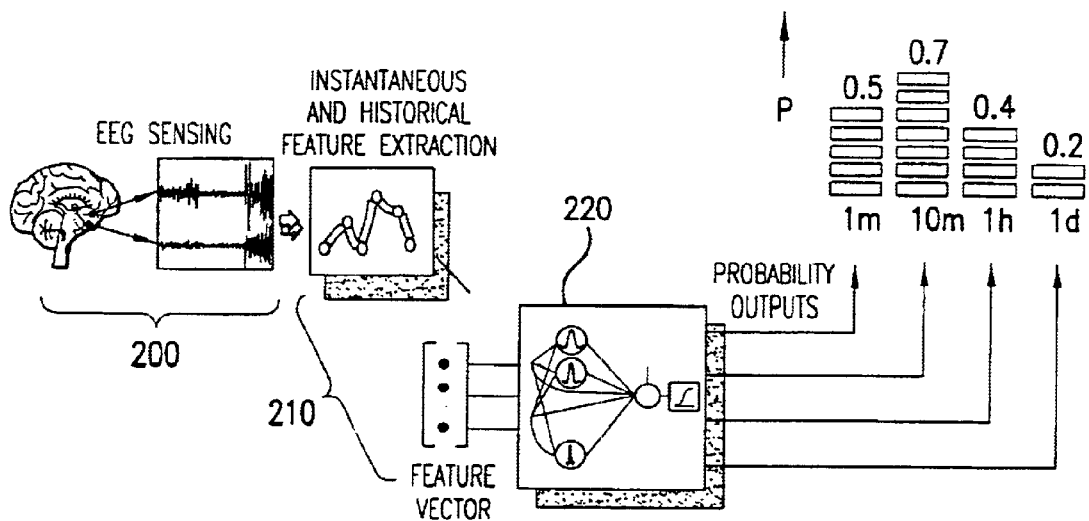
FIG. 4 is a generalized block diagram showing the overall process for predicting the onset of a seizure according to the present invention.

Referring to FIG. 4, the process flow according to the present invention will be described. At step 200, intracranial EEG signals or other physiologic signals are sensed by implanted electrodes or other appropriate sensors (that may not be implanted) and are pre-processed (amplified, filtered, multiplexed, etc.) by components in the implanted unit. In step 210, a processor preferably in the portable unit extracts premonitory signal characteristics to generate a feature vector(s). Next, in step 220, the feature vector(s) are processed by an intelligent predictor network, such as a wavelet neural network (implemented in either software or hardware), that continuously estimates the probability that a seizure will occur within one or more fixed or adjustable time periods. Examples of time periods are the next 1 minute, 10 minutes, 1 hour, and 1 day. The portable unit triggers visual displays and auditory cues of this information, and/or commands the implanted unit to administer abortive and/or mitigative therapy.

The signal processing required to extract the features and perform prediction is most likely performed in the implanted unit 102 due to its proximity to the brain activity or other physiologic signals. However, if the link 114 between the implanted unit 102 and the portable unit 104 is a type that can maintain a rapid upload of the physiologic signals from the implanted unit to the portable unit 104, this signal processing can be performed in the portable unit 104. This is a design consideration and is not critical to the basic concepts of the present invention.

Moreover, for some patients, the algorithmic complexity required for prediction may be such that prediction is achieved in real title on a powerful processor or computer not necessarily located in a miniaturized device (e.g. the implanted unit, although wearable computers are currently commercially available at 233 MHz processor speed/4 Gbytes total storage). The CPU-time hungry processes could be the learning phases and the extraction of some signal features. The probability estimation, on the other hand, is virtually instantaneous. Therefore, for the training/learning phase, most of the intelligence can be shifted away from the portable unit, if necessary, and into a computer workstation. The initial training can take place during pre-surgical evaluation, and periodic retraining can be accomplished during outpatient visits by hooking up the portable device to a docking station/desktop PC where the intensive programs run. The portable device uploads compressed past performance information, offline learning takes place on the PC, and refreshed parameters are downloaded back into the portable device at during an office visit, remotely via the Internet or via another type of communication device. The device can optionally carry out a form of online adaptation that is less demanding. For feature extraction processing, memory can be traded off for speed by pre-optimizing artificial features created as wavelet neural network (WNN) models on high-end computers. Feature extractors can then be hardwired into the device, such as by way of a WNN.

Figure 5:
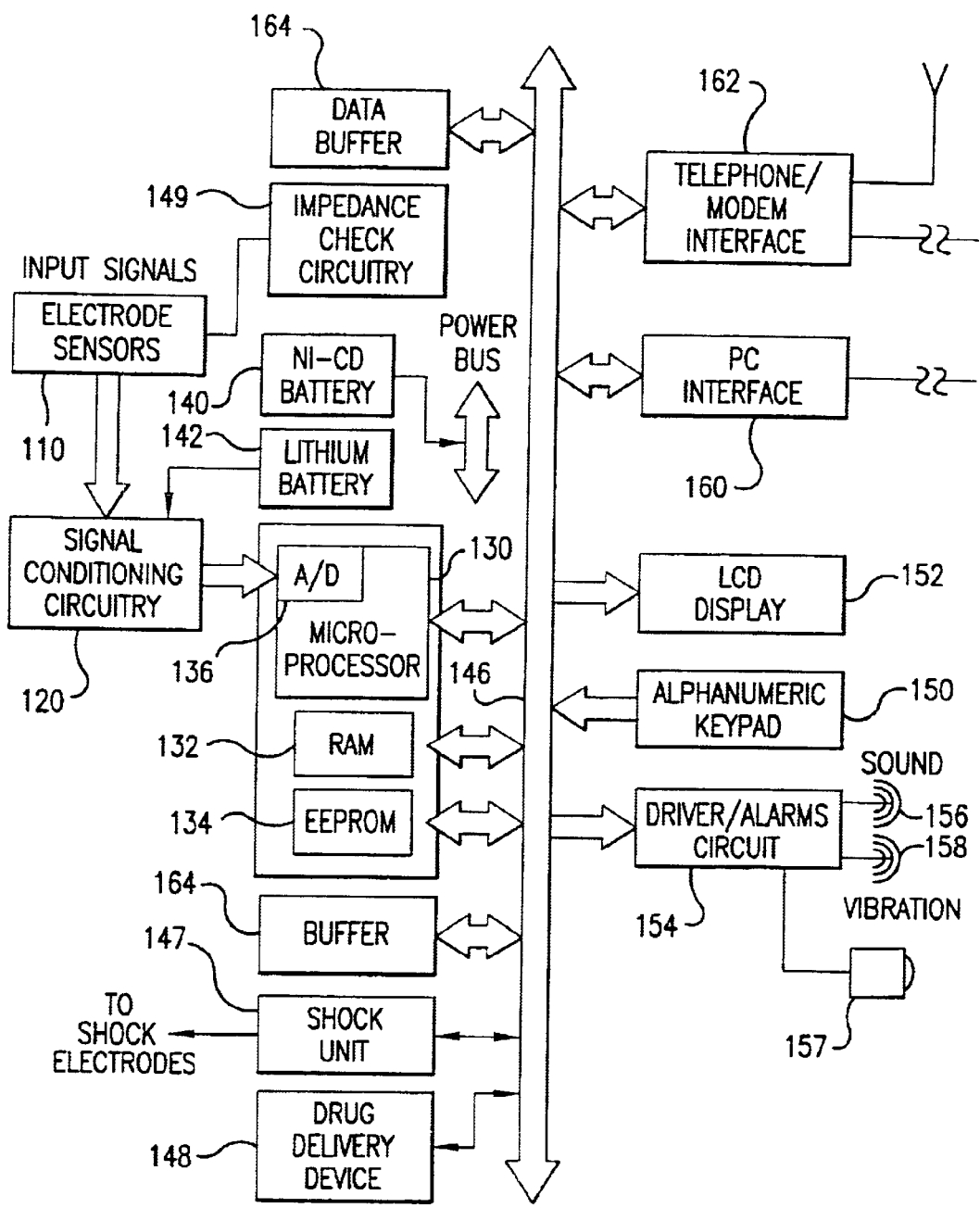
FIG. 5 is an electrical block diagram showing components of the system according to the invention.

Turning to FIG. 5, more details of the signal processing and related components that make up, in some combination, the implanted unit 102 and the portable unit 104, will be described. In one embodiment, the implanted unit 102 comprises signal conditioning circuitry 120, a microprocessor 130, random access memory (RAM) 132, electronically erasable programmable read only memory (EEPROM) 134, an analog-to-digital (A/D) converter 136, a rechargeable Ni—Cd battery 140 and a backup lithium battery 142. In addition, there is impedance check circuitry 149 to monitor the impedance of the electrodes to check for electrode integrity. A software diagnostic routine, executed by the microprocessor 130, checks for overall system integrity (including electrode integrity) at start-up and thereafter on a periodic basis.

The portable unit 104 comprises a keypad 150, a display 152 (such as a LCD), an alarm driver circuit 154 to drive an audible alert device 156, a visible alert-device (LED) 157, a vibration alert device 158, a PC interface 160, and a telephone/modem interface 162. The PC interface 160 facilitates communication with a PC 115 and the telephone/modem/network interface 162 facilitates communication with the Internet 118, telephone network (public, cellular or two-way messaging) or local network. Information is passed between the implanted unit 102 and the patient access unit 104 via the (data/address/control) bus 146 and over the link 114 (FIG. 3).

In addition, a data buffer 164 is included in either the implanted unit 102 or the portable unit 104 to collect brain activity or other physiologic data to be uploaded. For example, data from pre-ictal (pre-seizure) events are compressed and stored for periodic uploading either at a physician's office, via a PC, Internet or telephone, for periodic training updates.

As explained above, the components of the system 100 that are contained within the implanted unit 102 a biocompatible housing for implantation in a patient may vary. For example, it may prove more practical to include the feature analysis component(s) (i.e., the microprocessor 130) in that portion of the system not implanted within the patient. Moreover, all of the components of the system 100 may optionally be contained within a single housing that is implanted in a patient, and the system is programmed, monitored and tuned remotely by a suitable link. In this way, the system 100 cannot be accessed by a patient or other person that is unfamiliar and not comfortable with having direct access to the system 100.

The signal conditioning circuitry 120 performs data compression, amplification, filtering, isolation and multiplexing of the raw data signals from the electrodes 110. In addition, the signal conditioning circuitry 120 removes from the raw data signals drastic "artifacts" determined not to originate from brain activity. This is achieved using well known artifact rejection technology. After conditioning, the signals are converted to digital signals by the on-board AID converter 136 for temporary storage in the RAM 132 and further processing by the microprocessor 130. The microprocessor 130, through system parameters and software stored in the EEPROM 134, performs feature extraction and feature vector formation from the digital signals stored in the RAM 132, and also continuously analyzes/evaluates the feature vector with an intelligent prediction subsystem (implemented through software stored in EEPROM 134 or embodied as a separate network or device) to determine a probability of whether a seizure is impending (or is occurring) in the patient.

Alternatively, a digital signal processor (DSP), application specific integrated circuit (ASIC), field programmable gate array (FPGA), or other processing devices known in the art may be used in place of, or in addition to the microprocessor, to perform the feature extraction and analysis functions. It is further envisioned that in certain applications, all of the signal processing functions (pre-processing and feature analysis) be performed in a single programmable integrated chip or device.

The intelligent prediction subsystem may be implemented by a trainable network, such as for example, a wavelet neural network (WNN), and is trained with feature vectors to generate an output that consists of a probability measure within a predetermined period of time. A WNN is a special class of neural networks. A neural network is a mathematical construct composed of multiple layers of nodes that are connected together. Each node has an activation function and each connection between two nodes has a weight. The output of each node is a nonlinear function of all of its inputs. A neural network learns by approximating a multidimensional function over a space spanned by the activation functions for each node. WNNs are neural networks that employ activation functions, which are local and semi-orthogonal. WNNs are unique in that they can represent the behavior of a function at various resolutions of inputs. The efficiency and parallel distribution of computation units make WNNs ideally suited for implementation in a high-speed, portable hardware platform useful in the method and apparatus of the present invention.

The intelligent prediction subsystem is trained to minimize the expected value of a performance metric (after thresholding the output probability). As an example of one or many suitable performance metrics, a metric called the convexly weighted classification (prediction) accuracy (CWCA) is defined, equal to $\alpha CPR+(1-\alpha)CNR$, where CPR=fraction of times that the seizure is correctly predicted within the universe of imminent seizures (called sensitivity) and CNR is the correct negative rate, i.e., it is equal to 1 minus a false alarm rate. The weight $\alpha x$ on CNR depends on false alarm tolerance, where $\alpha$ is adaptively adjusted depending on an particular patient.

The intelligent prediction subsystem is trained with brain activity data, such as EEG data, or other physiologic data, "off-line" using a global training set of EEG data as well as EEG data for a particular individual for whom the system will be used. Specifically, in the "off-line" mode, features are extracted and selected using actual brain activity data for a particular individual to optimize the prediction capability and to minimize calculation and processing. The intelligent prediction subsystem is then trained based on that feature vector. Once the feature vector has been optimized and the intelligent prediction subsystem trained on that feature vector, the system is ready for "on-line" use for a particular individual. During the "on-line" operation, the system continuously processes real-time brain activity data from a patient, analyzes the data, makes a declaration of the probability of seizure onset on several time horizons (or a declaration of seizure onset if a seizure is occurring), and generates one of the possible outputs described above. Further, while "on-line," the intelligent prediction subsystem of the system may undergo further learning based on the real-time data to more finely tune to the brain activity characteristics of a particular individual. In addition, the intelligent prediction subsystem is designed to detect seizures, in the event of missed predictions, to automatically trigger a warning in response to detecting electrical onset of seizures. Patient interaction with the system in the event of false positive alarms will further facilitate "on-line" learning of the intelligent prediction subsystem. For example, the patient may flag that a seizure has occurred, and buffered data will be stored and labeled accordingly in the implanted unit. On periodic retraining, these flagged data will be inspected to verify that a seizure has indeed occurred, and then update training of the intelligent prediction subsystem will take place to reflect this occurrence, if necessary.

Initial training of the device may or may not have to take place at the hospital. In one scheme, the patient is admitted to the hospital, several seizures are recorded, and the device is trained for the first time. Subsequent periodic interactions of the device with a remote PC are made to further refine learning based upon periodically buffered data and events. Changes in anti-epileptic and other medications may require some retraining/learning as well. In a second scheme, the implanted unit is implanted and the patient is released from the hospital without initial recorded seizures and training. Seizure and pre-seizure data are buffered and periodic training is achieved offline on remote PC. This scheme may be preferable in some ways because spontaneous seizures recorded out of hospital may have different signal characteristics than those induced by rapid medication taper.

The system is programmable to respond to the output of the intelligent prediction subsystem to take one or more actions. For example, the microprocessor 130 may output a warning signal to trigger the driver alarm circuit 154 to activate the audible alert device 156, the visible alert device 157, the vibration alert device 158 and/or display a suitable warning message on the display 152. Cellular telephone and/or e-mail communication of this event may also be made, or data representing the event is stored for later transmission. The intelligent prediction subsystem may provide a continuous output representing a probability that a seizure is going to occur within a certain time horizon, or several continuous outputs representing probabilities for multiple time horizons. A warning can also be issued to others external to the individual patient when probability of a seizure exceeds a certain marked threshold over a certain time period (e.g. sending an alert to a child's mother, teacher or physician, etc.)

The system 100 may be programmed (through the keypad 150, for example) to set thresholds for certain alarms, such as display alarms, audible alarms, and vibration alarms. Once an alarm has been activated, further increases in the probability measure will be indicated by corresponding increases in alarm duration and intensity. The intelligence for interpreting the output of the intelligent prediction subsystem with various programmable thresholds may alternatively be included in a separate controller in the patient access unit 104, rather than in the implanted unit 102.

In addition, the microprocessor 130 may be programmed to activate one or more preventative therapies. For example, an electrical shock, series of shocks, pacing signal or particular stimulation patterns can be administered by a stimulation or shock unit 147 via electrodes positioned at locations in or around the brain known to effectively avert a seizure. Electrical shock delivery circuits for generating signals of suitable characteristics to prevent seizures are well known in the art. The shock scheme is one that is an intelligently paced stimulation as opposed to a thresholded shock or open-loop continuous stimulation (as in vagal nerve stimulator).

Some stimulation routines may be interactively modified in coordination with sensed brain activity after the system has predicted (or detected) a seizure based on probability measure output of the intelligent prediction subsystem. Alternatively, a single or multiple drugs or naturally occurring compound(s) may be automatically delivered into the patient by a drug delivery device 148 worn by or implanted in the patient. Body wearable or implanted drug delivery devices are well known in the art.

The therapeutic actions and the range of intensity of those actions may vary. For example, the system may be programmed to trigger only a mild type of intervention in response to a moderate probability warning issued for a long prediction time horizon. On the other hand, the system may be programmed to respond to high probability events for a short prediction time horizon with a more intense intervention. The system may be programmed to select intervention actions only in response to high probability-short prediction horizon events, particularly if the intervention that is effective for a particular individual is one that has significant side effects, such as drowsiness, etc. The continuous probability outputs, their integral, derivative, and/or any other mathematical derivations thereof may be used to intelligently grade the amount of intervention, particularly if probabilities increase and time horizons for prediction shorten over time.

The system may include a mechanism for a patient to manually flag when a seizure occurs. For example, a button may be provided on the portable unit to record that a seizure had occurred, even when the system did not predict it. Brain activity or other physiologic data sensed by the electrodes may be stored in memory for a predetermined time period prior to the false negative seizure event, to be downloaded (by phone, modem, etc.) to a monitoring center for further analysis. In this way, it is possible to record false negative predictions and more importantly, to obtain brain activity data that preceded the unpredicted seizure event so that the system can be retrained to predict the seizure more accurately. In addition, by permitting a patient to manually record what he/she believes is a seizure event, it is possible to diagnose events that the patient thinks are seizures but actually are not epileptic seizures.

The system may include the capability of communicating with persons other than the patient. For example, a cellular telephone, two-way pager, or other transmitter may be connected or interfaced with the portable unit to send seizure warning signals to a physician, family member, friend, etc. Similarly, warnings can be sent over the Internet (by way of e-mail or other instant messaging).

EXAMPLES OF USEFUL FEATURES AND HOW THEY ARE EXTRACTED

Features are quantitative or qualitative measures that are distilled from raw data and contain relevant information for tasks such as classification and prediction. In the classical pattern recognition field, feature extraction refers to good linear combinations of variables. Computational intelligence has given rise to other interpretations, such as considering a hidden layer in a neural network as a nonlinear feature extractor. In the medical field, "features" are often referred to as "parameters." In addition, some practitioners equate a feature with a single number (a scalar) while others equate it with an abstract quality that is measured using several numbers (a vector). For purposes of the present invention, a feature is defined as an individual variable. Thus, a "feature vectors" is simply a collection of features organized in vector form.

Figure 7:
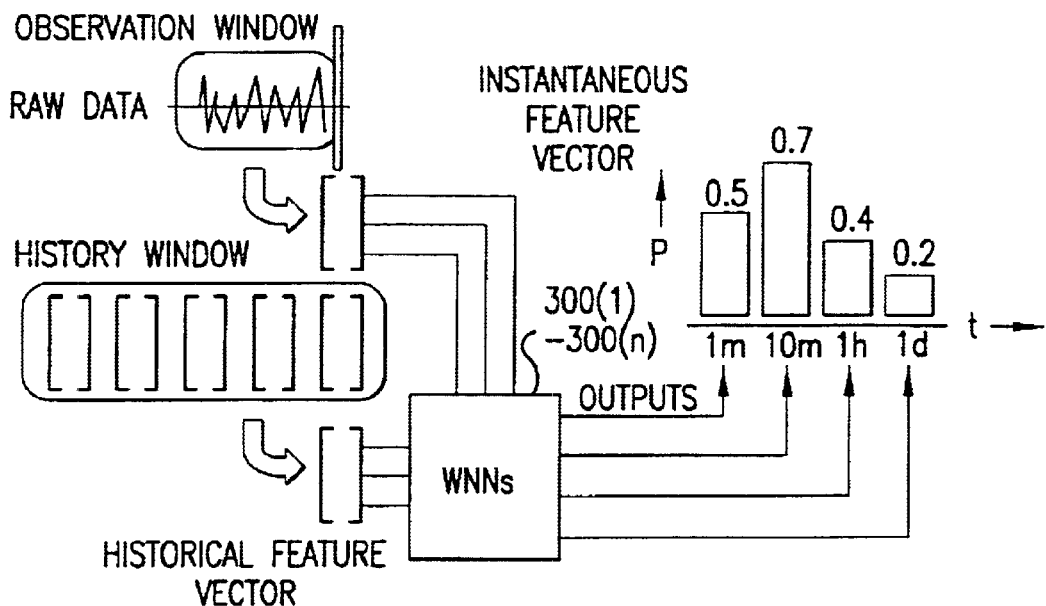
FIG. 7 is a diagram showing a scheme for analyzing features extracted from brain activity signals as a predictor of seizure onset and outputting a plurality of probability measures each for a corresponding prediction horizon.

A "feature library" is a collection of features which are extracted by algorithms from raw brain activity data. With reference to FIG. 7, there are two levels of features: instantaneous and historical. Instantaneous features are computed from observation windows that are essentially 1.25 seconds or less in duration. Historical features span longer periods, and are based on the evolution of instantaneous features, as shown in the FIG. 7. The feature vector is derived from the feature library.

Some examples of instantaneous features include: autoregressive coefficients, spectral entropy, coherence, cross-covariance, correlation between entropies, energy, energy derivative, entropy, filtered amplitude squared, fractal dimension, fourth power indicator (defined hereinafter), mean frequency, nonlinear decorrelation lag, nonlinear energy operator, number of zero crossings, Pisarenko harmonic decomposition, power distribution in frequency bands, principal components, principal Lyapunov exponent, real cepstrum, spike (occurrence, amplitude, curvature), third-order spectrum, wavelet subband energy, wavelet compression coefficients, epileptiform discharge complexity (a measure of number of peaks, amplitude, frequency content and morphology of spike waveforms), amount of back-ground disruption (amount of deviation from baseline time and frequency characteristics of electrical signals), regional coherence (coherence of activity in a focal brain region compared to that of other regions in the brain) and zero crossings of energy derivative. Since many features are widely known in the field, formulas are provided below only for new or less commonly known features.

Fourth Power Indicator.

$$P = \frac{1}{N} \sum_{n=0}^{N-1} dE[n]^4, \quad N = 10, \quad \text{overlap} = 5,$$

where energy derivative $dE[n] = E[n] - E[n-1]$.

Pisarenko Harmonic Decomposition. Absolute value of the first three coefficients (the next three magnitudes are reflected) of a fifth degree characteristic polynomial, $$\sum_{i=0}^{5} a_i z^{-i},$$

whose roots lie on the unit circle. The roots represent poles of a linear discrete-time system whose impulse response is a sum of sinusoids identified from the data sequence x[n]. The vector of coefficients $a_i$ is the eigenvector associated with the smallest eigenvalue of the 6×6 covariance matrix of the convolution matrix of x[n]. This is virtually identical to the rotation vector associated with the smallest singular value of the mean-removed embedding matrix of x[n] (principal state-space reconstruction with embedding dimension=6 and delay=1). A small difference between methods arises from the mean estimates.

Nonlinear Energy Operator. $NEO = x^2[n-1] - x[n]x[n-2]$.

Special Entropy (SE). SE provides a measure of organization in neural function which preliminary experiments suggest may be useful in seizure prediction and detection. As an example, a window length of 30 seconds is useful such that the data for each channel is divided into consecutive segments, $x_i$, of length N=2160 points with a 46% overlap.

First, the reference spectrum is found from:

$$P_i(\omega_k) = \frac{1}{N} |X(\omega_k)|^2$$

where $X(\omega_k)$ is the discrete-time Fourier transform (DTFT):

$$X(\omega_k) = \sum_{n=0}^{N-1} x[n] \exp(-j\omega nt)$$

A variety of windowing functions were evaluated to determine the best method for smoothing the processed signal. Ultimately, the periodograms were smoothed using a Bartlett window. The smoothed periodograms are represented by:

$$S_i(\omega) = \sum_u w_u P_i(\omega_{k-u})$$

The coefficients of the Bartlett window are:

$$\text{For } n \text{ odd: } w[k] = \begin{cases} \frac{2(k-1)}{n-1}, & 1 \le k \le \frac{n+1}{2} \\ 2 - \frac{2(k-1)}{n-1}, & \frac{n+1}{2} \le k \le n \end{cases}$$

$$\text{For } n \text{ even: } w[k] = \begin{cases} \frac{2(k-1)}{n-1}, & 1 \le k \le \frac{n}{2} \\ \frac{2(n-k)}{n-1}, & \frac{n}{2}+1 \le k \le n \end{cases}$$

The spectral entropy is then found to be:

$$H = -\sum_k S(\omega_k) \log_2 S(\omega_k)$$

Examples of historical features include those obtained from statistical process control charts for detecting special cause variability between observed subgroups: accumulated energy, cumulative sum, exponentially weighted moving average (EWMA), histogram, minimax (minimum and maximum of n standardized variables), np-chart (number of "defectives"), r-chart (range), s-chart (standard deviation), and xbar-chart (mean). Subgroups are obtained by successive nonoverlapping blocks (subgroup windows) of EEG instantaneous features (individual samples in each subgroup deployed through time), with subgroup sample sizes greater than or equal to 1. A second kind of subgroup can be obtained from an instantaneous single-channel feature applied across multiple channels (individual samples in each subgroup deployed through space). In its basic form, each point in the chart reduces the subgroup window of a given feature to a single number. The single number is, for example, the mean value of fractal dimension, or the standard deviation of energy, or the number of spikes within the subgroup window. When this number goes outside 3 standard deviations ($3\sigma$) above or below a center line, an "out-of-control" condition is recorded. The system estimates the center line and control limits from data under "in-control" (nonpreseizure) conditions.

Accumulated Energy (AE). The AE feature is extracted from the energy of the measured IEEG time series. If the IEEG sequence is denoted as $x(n)$, then the instantaneous energy of $x(n)$ is given by: $x^2(n)$. Using a sliding window, then the energy of the signal becomes an average energy:

$$E[n] = \frac{1}{N_1} \sum_{i=n-N_1+1}^{n} x(i)^2$$

where $N_1$ is the size of the sliding window expressed in number of points. AE contains historical information, and represents a discrete integral of the energy over time. It is calculated as follows. From the energy records obtained from expression above, a new moving average window of several points, such as 10, is slid through the energy record with an overlap of 5 points, and a new sequence is derived as the cumulative sum of these values. The equation below summarizes the mathematical computation of the AE:

$$AE[n] = \sum_{i=5(n-1)+1}^{5(n-1)+10} E[i] + AE[n-1]$$

In addition to the basic extreme pattern, there are other patterns in control charts that signal anomalies. Most are detectors of "non-randomness" based on counters. Examples include: 2 of 3 consecutive points outside $2\sigma$ limits, 4 of 5 consecutive points outside $1\sigma$ limits, 15 consecutive points within $1\sigma$ limits, 8 consecutive points on same side relative to center line, trend of 6 consecutive points increasing or decreasing, 14 consecutive points alternating between increase and decrease, periodicity, and number of extremes per history window. Binary sequences can be used to flag presence or absence of the patterns, or sequences can be left as "continuous" running counts. The history window is infinite for EWMA, larger than subgroup windows for counters, and equal to the subgroup window for each mean estimate of a feature.

Pre-ictal Prodromes. Pre-ictal prodromes are specific pre-ictal patterns which occur on the EEG, either visible to the eye or only discovered computationally, which build prior to and herald seizure onset. They may increase in their frequency of occurrence, their amplitude or their duration as a seizure approaches.

In addition to preexisting features, an optimal set of artificial features customized for a particular patient and/or prediction task can be constructed. Given a set of features, it is known how to prescribe optimal classifiers and how to create near-optimal ones empirically using neural networks. However, the power set of these features may not convey maximum information available in the raw data. The act of prescribing the features themselves is routinely dismissed as an "art"—an inductive problem guided only by trial-and-error or intuition of the physics.

The following terminology: feature extraction, feature creation, feature optimization, feature learning, feature optimization, feature discovery, feature mapping, feature augmentation, feature transformation, and signal or data projection, appears in the prior art in contexts that always boil down to working with the same finite set of pre-chosen features:

(1) selecting a feature subset from a predefined list with methods such as forward and backward sequential selection, or combined add-on/knock-out, (2) creating features as linear combinations of input features (the classical definition of feature extraction) such as principal components, or creating feature vectors as linear combinations of raw inputs with methods such as adaptive noise filtering and time-frequency transforms, (3) creating features as nonlinear combinations of the input features considering a hidden layer in a neural network as a nonlinear feature extractor, or joining inputs by algebraic operators.

Recognition rate improvements obtained from these methods stem from refining the decision structure by making patterns more obvious, and not from creating new information; derived features cannot contain more information than is already hidden in the original set. The art of specifying the original features comes from the fact that they are somehow "chosen" from an infinite list. A heuristic approach is proposed that amounts to searching in this much larger space of possible features.

If performance depends so much on input features, the challenge is to decide where to draw the line between the features and the predictor structure. In the present invention, the line is initially drawn as far back as the raw data. Learned artificial features are customized for the given task, and presented to a predictor structure as if they were conventional features computed procedurally. This is based on the following observation: Since a feature (quantitative or qualitative-turned-quantitative) is obtained from a formula or algorithm that maps a raw input set into a scalar, then a neural network is capable of learning and implementing the map.

Figure 6:
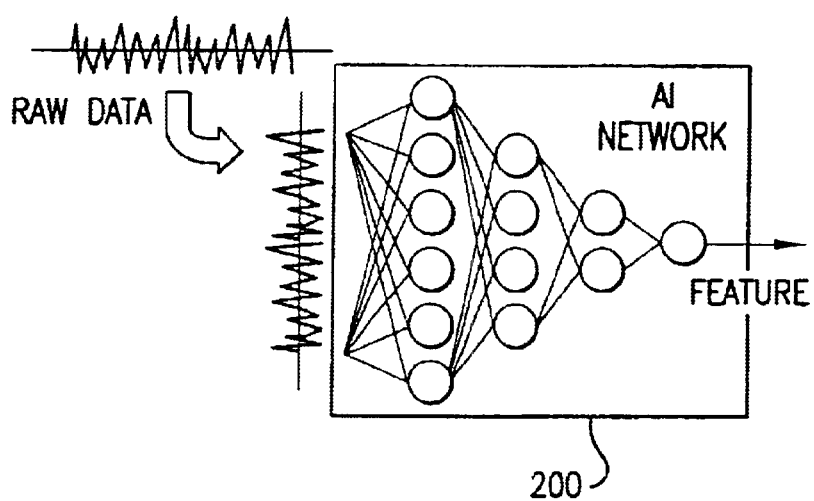
FIG. 6 is a diagram illustrating the creation of neurally computed (artificial or conventional) features according to the system and method of the present invention.

As shown in FIG. 6, an artificial intelligence (AI) network 200 is employed to generate the feature vector. The neurally computed features are the outputs of feedforward networks, or the stable equilibria of recurrent networks, and can mimic conventional features or be artificial features altogether. Recurrent WNNs may yield more compact solutions at the expense of additional training and stability considerations.

The learning phase required for neural computation of features commands a great deal of computational resources for a large-sized input array, therefore reaping the full benefits of this method involves the following prototypical situation. Group A has a technical prediction problem and either the current solution is unsatisfactory or an improvement is sought. A raw database is sent to a high-performance computing facility where group B synthesizes a set of artificial features off-line, customized for group A's problem within stipulated time and computer capability constraints. The result is downloaded back to group A as a "black box" of pre-optimized features, which are then neurally computed on-line. By definition, the only way for group A to further improve performance (if at all possible) is by looking for different or additional raw measurements.

Artificial features can be synthesized from unsupervised learning, reinforced learning, and supervised learning. For example, for supervised learning, it is clear that the single best artificial feature is the output of the final predictor itself—it compactly conveys the premonitory class or probability information—but that is precisely the unknown when the problem is first tackled. An off-line training session using desired targets as outputs taken this far produces a complete solution in a single WNN. In this case, the input feature and the prediction output are the same thing. Typically, however, the off-line synthesis is subject to time constraints and a sub-optimal output will be produced. This resulting artificial feature (or feature vector), being already close to the desired solution, is better suited than conventional ad-hoc features for later training of the predictor structure chosen by the user. This is somewhat similar to the way in which the known Group Method of Data Handling composes the desired output solution by using ever closer partial solutions as inputs.

Neurally computed features are fed as input features to the predictor structures. Under certain conditions it is advantageous to compute features neurally as opposed to procedurally, even when the features are not artificial. For example, the computation of correlation dimension $D_c$ (a measure of fractal dimension found to be valuable in seizure detection and prediction) involves many steps: sequentially hypothesizing embedding dimensions, computing pairwise distances, extracting and offsetting the IEEE-standard exponent of 32-bit floating point numbers, binning distances to obtain a correlation integral, fitting least-square-error lines to read dimensions off the slopes, and averaging results to reduce variance. The whole process is a transformation of vectors (e.g., 256-points long), to scalars that are only valid in the range of about 0.5 to 3.5. This procedure makes the $D_c$ feature very impractical for real-time implementation, but a neural version of it is useful in accordance with the present invention.

FEATURE SYNERGY, SUBSET SELECTION AND FUSION

The focus of seizure prediction research to date has been on finding a single feature (or multiple channels or multiple frequency bands) that by itself will give off a clear premonitory signal. Retrospective examination of features has shown promise but no perfect consistency has been found for any one feature acting alone in discriminating between the pre-seizure state and baseline EEGs. Since pre-ictal changes in raw EEG are notoriously elusive even to the trained electroencephalographer's eye, it is not surprising that any arbitrary single feature is not fully predictive. A single feature is a partial descriptor of underlying EEG, and all that can be seen from its temporal plot is a one-dimensional projection of its amplitude evolution folding upon itself. Higher dimensions in feature space are required to consistently detect subtle changes prior to seizure. The present invention introduces the use of feature synergism, wherein multiple features of a different nature and singly inconsistent, are together combined in a particular manner to increase consistency.

Many of the features in the feature library can be redundantly correlated to others, or can be completely irrelevant for the particular prediction task. Furthermore, the use of all features in the library places a large computational burden on the learning and analysis of the system. Therefore, a feature vector comprises a subset of features in the feature library. There are $$\binom{N_f}{n} = \frac{N_f!}{n!(N_f-n)!}$$

possible ways of choosing n-dimensional feature vectors from the universe of $N_f$ features, $n \leq N_f$. This can grow so large that exhaustive search becomes prohibitive. For example, $$\binom{30}{5}, \binom{30}{10}, \binom{100}{5}, \text{ and } \binom{100}{10}$$

yield 142, 506, $30(10)^6$, $75(10)^6$, and $1.7(10)^{13}$, respectively, ways of choosing a feature vector. An expedient strategy to deal with this exponential explosion is to find the smallest feature subset that "works" through a forward sequential search. Improved versions of sequential search, such as add-on-knock-out algorithms may be employed.

During the "off-line" analysis, each of the $N_f$ features derived from actual brain activity for an individual, are first individually scored based on validation error as explained hereinafter. The scores are sometimes given as distinguishability measures based on Gaussian assumptions about the one-dimensional conditional distributions $p(x|S)$ and $p(x|NS)$ of each feature. However, the features may be multimodal and overlap in ways that require more than one separatrix point. Thus, the preferred method is to score features based on performance on actual system outputs. After the first round of $N_f$ scores, the best one is made a permanent part of the feature vector. On the second round, the still unused feature that works best in conjunction with the first one is found. The process is iterated until n features have been chosen (prefixed or until scores exceed a desired level). This technique requires only $nN_f-n(n-1)/2$ scores. The numbers in the previous example reduce to 140, 255, 490, and 955, respectively. The predictor found with the best feature subset is deemed the final trained model. Training of the intelligent prediction subsystem is explained hereinafter.

Feature fusion refers to the way in which features are combined before reaching a prediction decision. Feature fusion is accomplished by presenting the features in parallel to the system. In an alternative embodiment of the invention, features are fused using active perception (See, I. Dar, *An Intelligent Sensor Fusion Approach to Pattern Recognition with an Application to Bond Validation of Surface Mount Components*, doctoral dissertation, Georgia Institute of Technology, September 1996) and Dempster-Shafer theory (See, G. Shafer, *A Mathematical Theory of Evidence*. N.J.: Princeton University Press, 1976). To arrive at a prediction, features are presented to the corresponding one-dimensional WNN classifier one by one. Given the ith feature x, the output of the WNN predictor is an estimate of the conditional pre-seizure class probability $P_T(S|x)$. A mass function can be derived from this information and the probability values can be assigned to the singleton classes pre-seizure (S) and nonpreseizure (NS), and zero to all other subsets of the frame of discernment (null and all). This vector is renormalized, if necessary, so that the sum of the masses equals 1 as required in Dempster-Shafer theory. From the $2^{nd}$ feature forward, the mass function represents an accumulation of evidence between the new evidence presented by the ith feature and all previous ones via Dempster's rule of combination. The degree of certainty (DOC) distribution is computed after presentation of each new feature. After enough evidence has been processed to reach a preset DOC level, the classification is the class whose DOC is maximum. The DOC computation is explained in H. Kang, J. Chang, I. Kim and G. Vachtsevanos' "*An Application of Fuzzy Logic and Dempster-Shafer Theory to Failure Detection and Identification*," IEEE Proc. $30^{th}$ Conf. Decision & Control, Brighton, England, pp. 1555–1560, 1991.

WNN PREDICTOR SYNTHESIS

Evidence suggests that there are pre-ictal changes in EEG signals which herald evolution toward a seizure. Consequently, it is more useful to define the outputs of the system to indicate an expected time of seizure onset and the degree of confidence or probability that a seizure will occur within that time period.

For example, as shown in FIG. 7, a prediction horizon can be divided into 4 prediction horizons: 1 minute, 10 minutes, 1 hour and 1 day. A probability P that a seizure will occur is generated by different WNNs trained for each of the four prediction horizons, where for the 1 minute horizon, P is 0.5; for the 10 minute horizon P is 0.7; for the 1 hour horizon, P is 0.4 and for the 1 day horizon, P is 0.2. This time-oriented probability measure or predictor is described in more detail hereinafter in conjunction with FIG. 8. In general, there are N number of WNNs employed, where N is the number of prediction horizons for which a probability measure is to be output.

Figure 8:
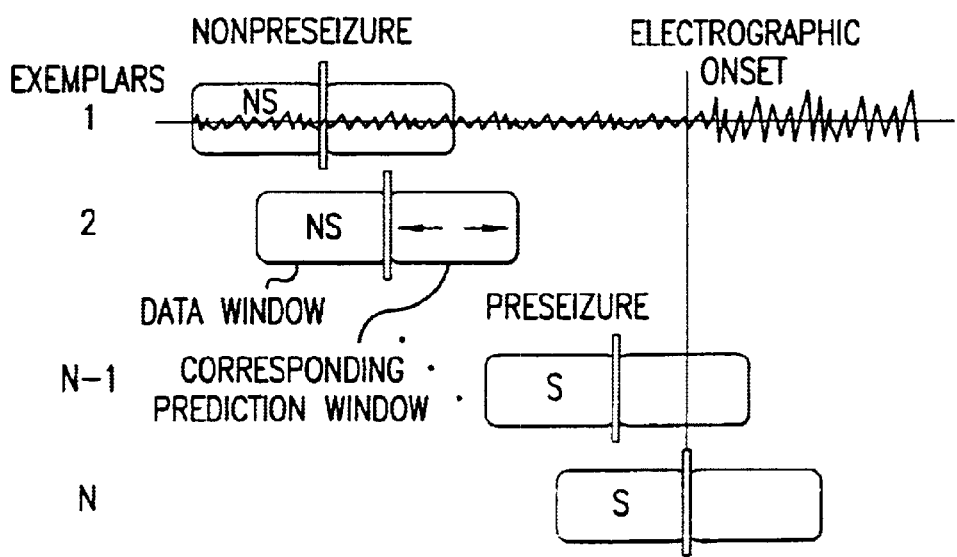
FIG. 8 is a graphical diagram illustrating the identification of pre-seizure or non-pre-seizure events with respect to seizure onset.

More generally, with reference to FIG. 8, the prediction output is defined to be the conditional probability $P_T(S|x)$, that is, the probability that one (or more) seizure(s) will occur at any time within the next T minutes, given the observed measurements x. This formulation allows for both a "hard" prediction (using a threshold on the output), and a measure of certainty regarding the imminent seizure event (the unquantized output). The WNN learns an estimate of the $P_T(S|x)$ function from data even though the desired target probabilities are unknown. All that is required is that the desired outputs be labeled as 1 for pre-seizure and 0 for non-pre-seizure (instead of actual probabilities), and that the WNN be trained using a least-squares error criterion with a logistic sigmoid in the output unit. It can be shown that this amounts to a logistic nonlinear regression that gives an estimate of probability in the output independently of feature distribution. As shown in FIG. 8, data are labeled as pre-seizure (S) and non-pre-seizure (NS) classes. All 30-minute periods beginning with each marked electrographic onset are dropped from the database for prediction purposes, since by definition they represent non-predictive data that corrupts the sought-after dependencies.

From the above considerations, the basic implementation of a T-minute WNN predictor is a multiple-input, single-output transformation:

$$\hat{P}_T = \frac{1}{1+e^{-u}},$$

$$u = \sum_{j=1}^{M} c_j \psi_{A_j, B_j}(x) + c_l^{lin} x_l + \ldots + c_n^{lin} x_n + c_0^{lin},$$

$$\psi_{A_j, b_j}(x) = \psi(\sqrt{e}, \text{rad}\ (x-b_j) A_j (x-b_j)^T),$$

$$\psi(x) = \min\{\max\{\tfrac{3}{2}(1-|x|), 0\} 1,\} \cos(\tfrac{3}{2}\pi x),$$

where x is a row vector of inputs $[x_1 \ldots x_n]$, $b_j$ is a translation vector associated with the jth wavelet node, $A_j$ is a symmetric positive semi-definite squashing matrix, and M is the number of wavelet nodes. The dependence of this WNN on T is implicit by way of the training data set that is used to tune the network parameters $A_j$, $b_j$, and c.

Figure 9:
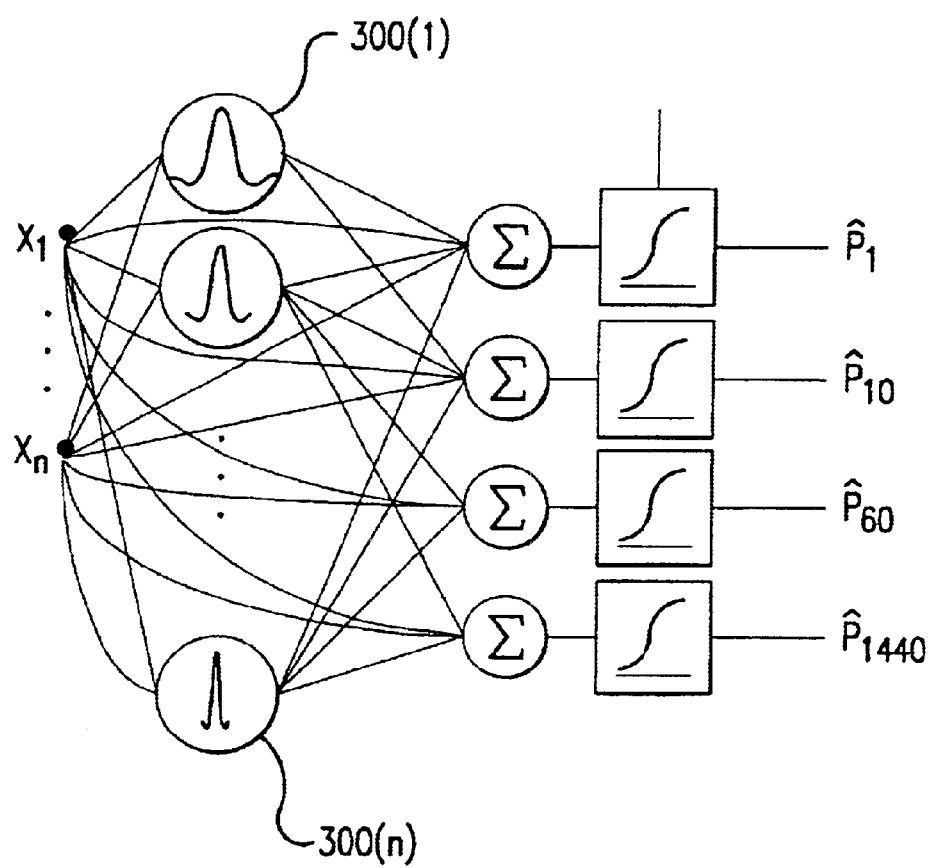
FIG. 9 is a functional diagram of a wavelet neural network for analyzing a feature vector and outputting a plurality of probability measures as shown in FIG. 7.

FIG. 9 shows a functional layout of WNN modules for analyzing a feature vector $\{X_1 \ldots, X_n\}$. Wavelet nodes 300(1)–300(n) connecting to each output P (with the subscript indicating the number of minutes in prediction horizon) may be shared. If it is chosen to implement the intelligent prediction subsystem without sharing nodes, then the WNN module is effectively 4 separate WNNs, each trained on a corresponding prediction horizon. The number of prediction horizons and their corresponding time interval may vary.

The number of wavelet nodes M is systematically found based on K-means clusterings of the training data in the input-output space for a successively larger number of clusters. Each clustering is assigned a measure of within- to between-variance of the clusters. The measure is the inverse of a multidimensional F-ratio, $$S = \frac{\sum_{i=1}^{K} \sum_{j=1}^{N_i} \|w_j^i - \overline{w}_i\|^2 / (N-K)}{\sum_{i=1}^{K} N_i \|\overline{w}_i - \overline{w}\|^2 / (K-1)},$$

where N is the number of exemplars, K is the number of clusters, $w_j^i$ is an input-output data point $[x\ y]$ that belongs to the ith cluster, $N_i$ is the number of such points in the ith cluster, $\overline{w}_i$ is the center of the ith cluster, and $\overline{w}$ is the grand mean. The number of wavelet nodes is taken to be the minimizer of the S function above.

For any given hypothesized WNN structure, training of the network parameters $A_j$, $b_j$, and c is cast as a minimization problem with respect to the empirical average squared error function $$ASE = \frac{1}{N} \sum_{i=1}^{N} \left(y_i - \hat{P}_T^{(i)}\right)^2,$$

where $y_i$ are labels in $\{0,1\}$. This criterion is used as a guide during minimization using the training set; however, care is taken to select a model that minimizes the expected value of this measure not over the training set, but over all future data. Estimates of the latter can be obtained in principle from regularization or resampling techniques.

From a practical point of view, split-sample validation is by far the simplest effective technique for preventing overtraining of the network and thus preserving generalization. The data set is split into a training set TRN and a validation set VAL (and optionally a test set TST; typical proportions are 60%, 20%, 20%). Training proceeds by minimization of error over TRN while monitoring the error on VAL. The best WNN on VAL is recorded at every iteration. Typically, the error over TRN drops to arbitrarily small values (provided a complex enough WNN), while the error over VAL first decreases and then increases steadily. The final network chosen is the one that minimizes the error over VAL, which is a form of early stopping during training. Note that minimizing VAL error in this fashion is not the same as overtraining on VAL (which can always be driven to zero). VAL is ideally a representative sample of the universe of all future exemplars. There is a bias introduced by this scheme to the extent that VAL deviates from this ideal. Using yet another unseen data set TST, a final test is usually run for assessing the generalization error. The actual minimization algorithms employed, such as Levenberg-Marquardt and genetic algorithms, are well known to those skilled in the art.

In order to obtain binary type alarms, thresholds are set on the continuous probability outputs. Alternatively, other methods may be suitable. A classification model can be obtained by quantizing the output of a probability model, however, such quantization is most useful for gauging the final performance of the probability model. The classification model can be trained directly as a classifier with a hard limiter in place of the sigmoid output unit:

$$C_T(x) = (u),$$

where u has the same form as that noted in the above equation and H(u) is 1 for $u \geq 0$ and 0 otherwise. In this case, the classification model synthesis is cast as a minimization problem with respect to the empirical average misclassification error (AME), which is the overall fraction of wrong predictions:

$$AME = 1 - OCR = \frac{N - N_{CS} - N_{CNS}}{N},$$

where OCR=overall correct rate, $N_{CS}$=number of correctly predicted positives, $N_{CNS}$=number of correctly predicted negatives, N=total number of seizure and no-seizure examples. The expected value of this quantity can be minimized using a genetic algorithm and a split-sample validation strategy. Other error metrics that assign different weights to false-alarm rates and prediction-to-onset times (like a negative detection "delay") may be used as well.

The following are practical examples showing how to implement probability estimators using WNNs with synthetic and real data.

In a first experiment, 200 samples of a normally distributed feature with two different means conditioned on equiprobable states were used to train a WNN with logistic output. The {0,1} target outputs were pre-warped as—log $(1/((1-2\epsilon)y_i+\epsilon)-1)$ (numerical inverse of the logistic function) to obtain a better initialization from that provided by the equation for S above. A Gauss-Newton method was used to solve the nonlinear least squares problem. Requiring only the linear portion of the WNN for this task, the correct probability function was very easily found.

Next, the experiment was repeated with an accumulated feature that resets itself every 10 minutes. Under simulated baseline-state, the feature increased linearly in the range [1,100]. Under a simulated pre-ictal state, the feature increased linearly from 1 to 49.5 during the first half of time, and from 49.5 to 150 during the second half. A challenge of this feature is that it behaves identically during both the first half of a pre-ictal and any non-pre-ictal period. The conditional density $p_{10}(x|S)$ is uniform with height 1/99 between 1 and 100. The conditional density $p_{10}(x|S)$ is piecewise uniform with height 1/99 between 1 and 49.5, and height 0.005 between 49.5 and 150. Then from Bayes' rule, the theoretical class conditional probability function for this problem is:

$$P_{10}(S|x) = \begin{cases} 0.5 & 1 \leq x < 49.5 \\ 0.33 & 49.5 \leq x < 100 \\ 1 & 100 \leq x \leq 150 \end{cases}.$$

Figure 10:
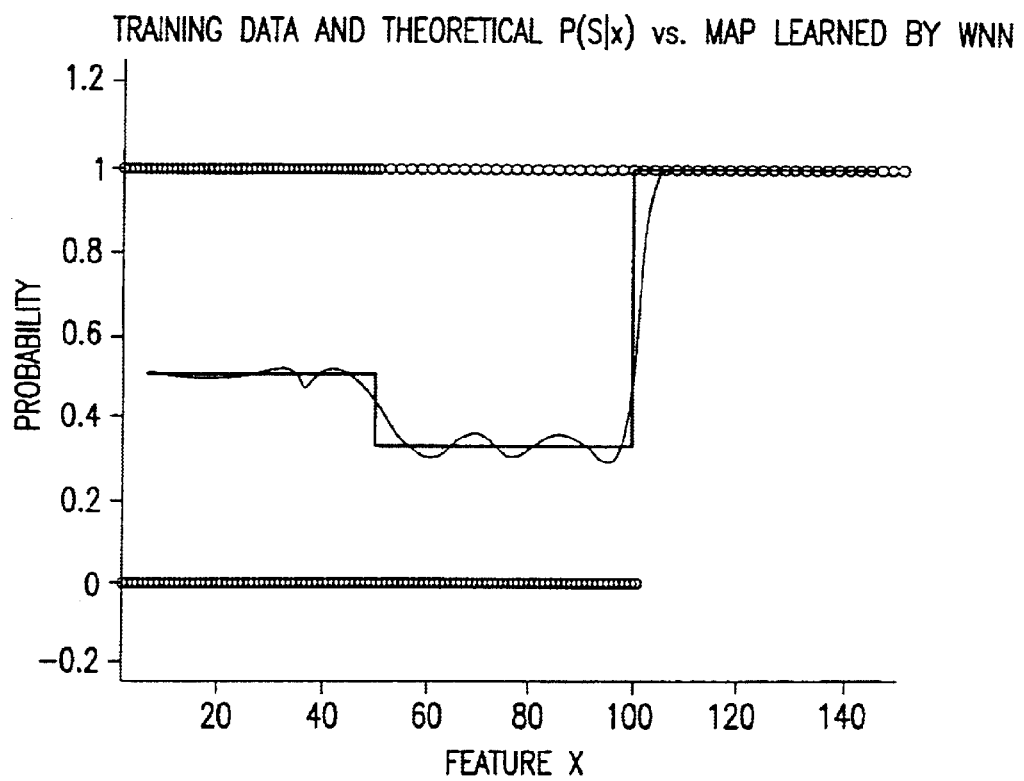
FIG. 10 is a graphical diagram showing the theoretical class conditional probability function useful in implementing a predictor using wavelet neural networks.

FIG. 10 shows this function, along with the approximation learned by a 4-node WNN. Since the distinguishing behavior of this feature is that it doubles its slope halfway before seizure and it reaches amplitudes never seen under baseline, then prediction with 100% certainty can be made with the theoretical or the WNN model, but the prediction-to-onset time (PTOT) cannot be earlier than 5 minutes. The average case is PTOT=2.5 minutes, when the resetting time of the sawtooth exactly matches the start of the 10-minute preictal period. The worst case is PTOT=0, in which case the predictor degrades to a (best possible) seizure detector.

The a priori probability of seizure is estimated as $P_T^{TRN}(S)$ from the proportion of pre-seizure examples in the training database. If this proportion does not reflect the true frequency of occurence $P_T^{true}(S)$ in the continuous time line, the estimate of posterior probability given by probability models will be distorted. According to Bayes' rule, the WNN probability estimator should learn the function $$P_T^{TRN}(S|x) = \frac{p_T(x|S)P_T^{TRN}(S)}{p_T(x|S)P_T^{TRN}(S) + p_T(x|NS)P_T^{TRN}(NS)}.$$

The conditional densities p(x|S) and p(x|NS) could in principle be obtained without regard to the proportion of examples under each class in TRN, and plugged in as two separate WNNs. Due to the denominator, rescaling the estimate $P_T^{TRN}(S|x)$ learned from training data by the factor $P_T^{true}(S)/P_T^{TRN}(S)$, where the true a priori estimate is learned over larger patient monitoring periods, is not sufficient either to correct the estimate and or to obtain $P_T^{true}(S|x)$.

Dividing numerator and denominator we obtain $$P_T^{TRN}(S|x) = \frac{1}{1 + \frac{p_T(x|NS)P_T^{TRN}(NS)}{p_T(x|S)P_T^{TRN}(S)}}$$

$$= \frac{1}{1 + \exp\left\{\ln\frac{p_T(x|NS)P_T^{TRN}(NS)}{p_T(x|S)P_T^{TRN}(S)}\right\}}$$

$$= \frac{1}{1 + \exp\left\{-\left[\ln p_T(x|S) - \ln p_T(x|NS) + \ln\frac{P_T^{TRN}(S)}{P_T^{TRN}(NS)}\right]\right\}}.$$

It is evident that the task of the WNN prior to the logistic output unit is to approximate the term between square brackets: a log-likelihood ratio function plus a bias. Therefore to correct $P_T^{TRN}(S|x)$ after having already trained the network, it is not necessary to retrain or scale the output, but rather go inside the WNN and replace the constant bias $c_0^{lin}$ in the linear combiner unit with $\ln(P_T^{true}(S)/P_T^{true}(NS))$. The bias term $c_0^{lin}$ in was verified to be the correct value (zero) in all our equiprobable experiments.

This observation is particularly important in seizure prediction because seizures are relatively rare events and $P_T^{true}(S)$ tends to be very small (for 2 weeks of data and a 10-minute prediction horizon, $P_T^{true}(S) \approx 0.005$). Training the network with such an unbalanced proportion of examples would obscure the very patterns it must pay attention to. Without loss of generality, a balanced set can be trained, injecting the unbalanced bias term later, and slowly tuning online if necessary.

The last experiment was repeated, this time with real data for all eleven 10-minute pre-seizures available for one of the patients in our database. Eleven profiles of accumulated energy were computed for these pre-seizure periods, and eleven additional profiles under non-overlapping 10-minute baselines (>8 hrs. away from onsets) with random starting times. Profiles were subsampled to 120 points. One of the profiles under each condition was blindly reserved for testing, and the remaining ten were used to train a 4-node WNN. The resulting bias term $c_0^{lin}=0$ was replaced by $\ln(0.005/(1-0.005))=-5.29$ as discussed before. FIG. 10 shows that high certainty prediction was possible in 9 out of the 11 pre-seizures with no false alarms. The best PTOT case can always be achieved by monitoring not a single accumulated energy in time, but the entire profile with each slide of the window. Features of this profile are then used to train the WNN probability estimator.

By providing as output a time-based probability measure, a patient or physician may set thresholds for the probability of a seizure over a prediction horizon. Thus, the system can be programmed as to when, whether and how the system will issue an alert. The patient can then take suitable action to prepare for the seizure such as staying in a safe and familiar environment until the period of high probability (i.e., greater than 50%) passes, alerting a physician, manually administering a drug, etc. In addition, the system is programmable to determine when, whether and how preventative actions are automatically taken to stop or prevent a seizure by way of shock therapy, drug delivery, etc.

The feature generation and analysis process used in the system and method according to the present invention is similar to that used in statistical process control (SPC) for engineering and industrial control applications. That is, the methodology of the present invention involves monitoring a parameter or statistic (brain activity features) with respect to a set of thresholds (control limits) in order to distinguish variability due to common causes as opposed to special causes (abnormalities). Persistent deviation of a parameter outside of its control limits signals a developing change in the process, analogous to the prediction of a seizure.

EXAMPLES OF USEFUL FEATURES FOR SEIZURE PREDICTION

The following discussion is directed to the utility of various features for predicting the onset of a seizure. Two or more of these features may be fused into a feature vector to train a intelligent prediction subsystem to predict a seizure.

Figure 11:
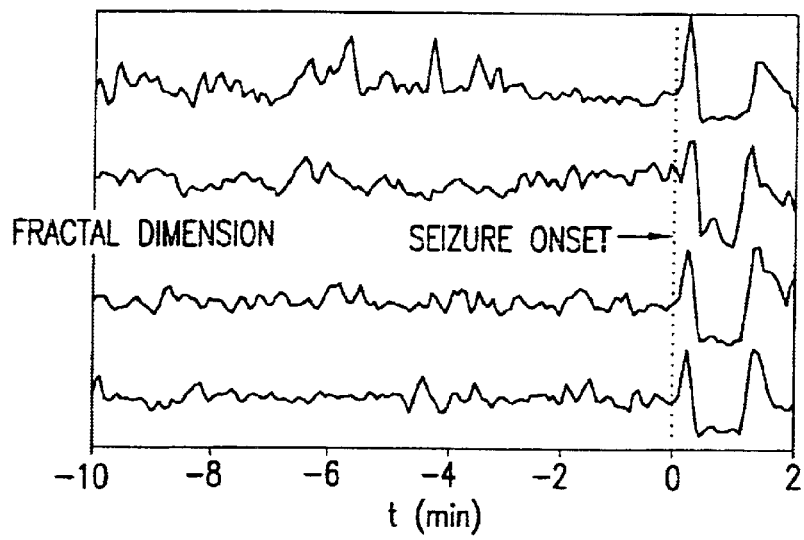
FIG. 11 is a timing diagram of a fractal dimension feature, exemplifying the utility of a single feature that may be predictive of seizure onset in some patients.

FIG. 11 illustrates one representative parameter, fractal dimension, for four seizures recorded from the same depth electrode in a patient. As with other parameters measured or calculated, seizure onsets had a characteristic appearance, with minor variation. Thus, in several patients with mesial temporal onset originating in one region, the computational burden for seizure detection and prediction may be reduced by tuning the intelligent prediction subsystem to brain activity characteristics specific to particular individuals. This feature is also useful to detect seizures with great rapidity and accuracy at the time of electrical onset.

Figure 12:
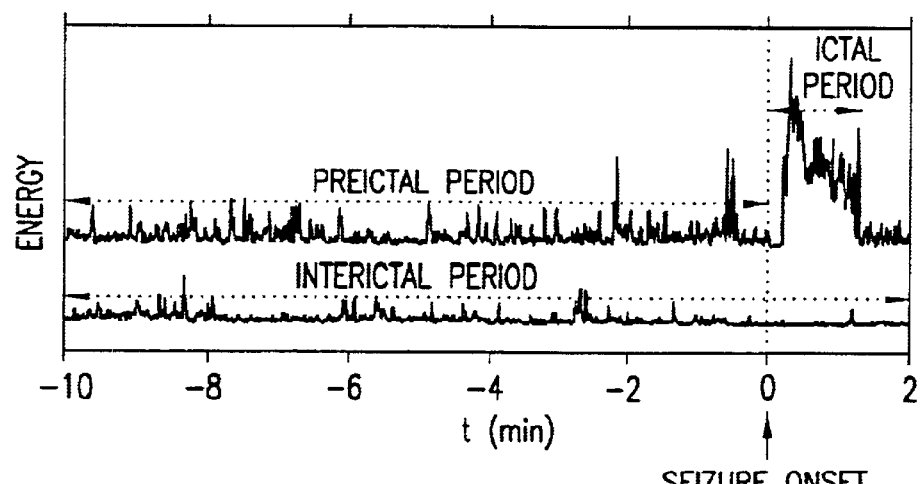
FIG. 12 is a timing diagram of an energy feature that can be monitored for early prediction of seizure onset in some patients.
Figure 13:
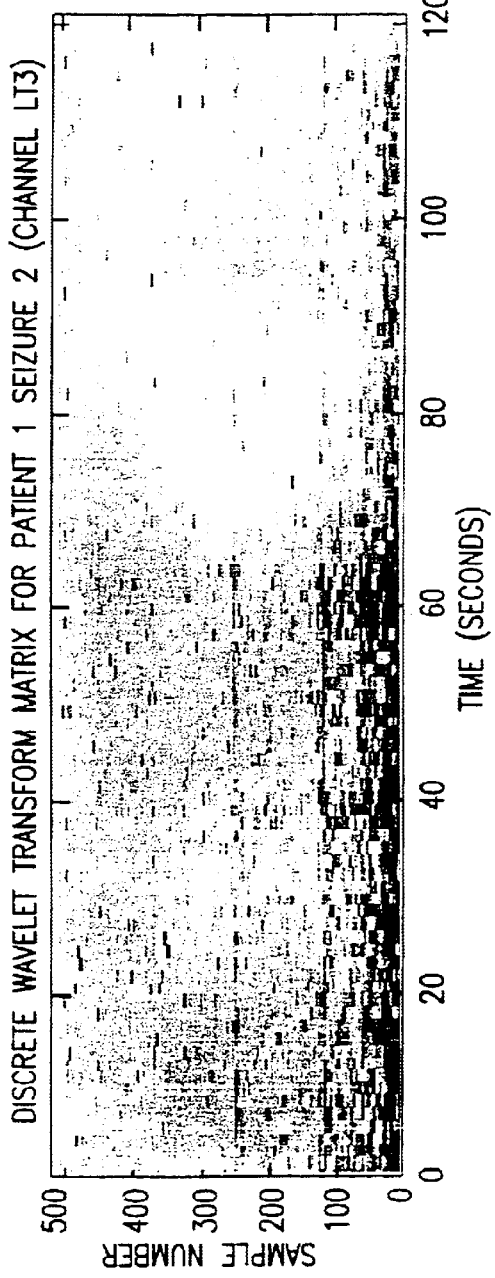
Figure 14:
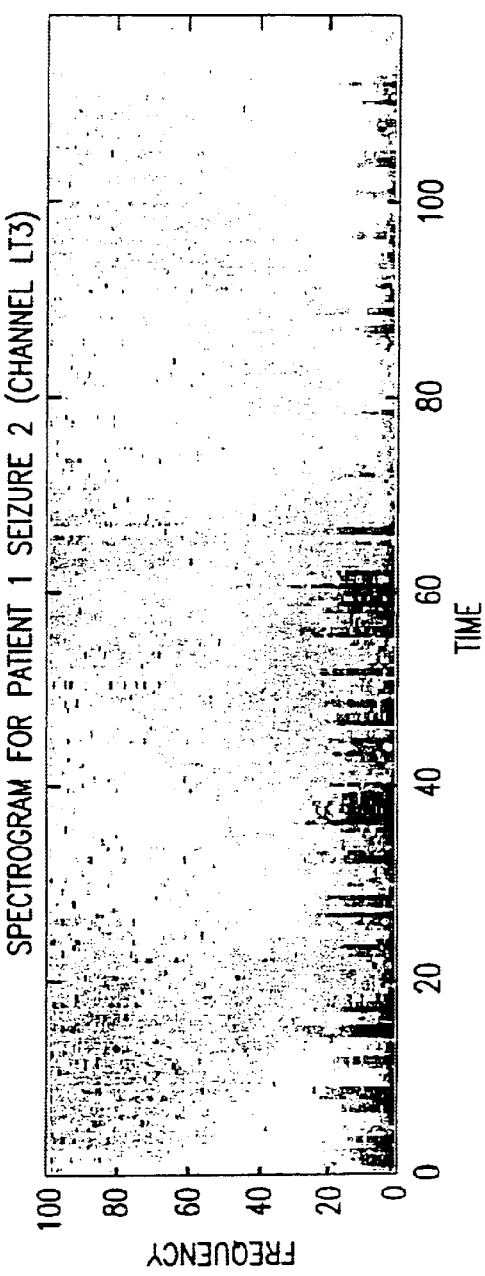

FIG. 12 illustrates a comparison of signal energy during a ten minute interictal period, 24 hours removed from any seizures, to a period of time leading up to a seizure, eight minutes prior to ictal onset. Two interesting features recorded during these two periods of time are the amount of total energy and frequency of peaks of energy prior to seizure onset. There are clear bursts of activity approximately two minutes prior to onset. A pre-ictal increase in baseline activity is consistent with information learned from patients when they seem to know when a seizure is impending. This suggests the utility of a method for predicting the probability of seizure onset in real-time, based upon accumulated measures of several parameters, including energy.

FIGS. 13–16 show plots of the time varying discrete wavelet transform (FIG. 13), spectrogram (FIG. 14), energy (FIG. 15), and entropy (FIG. 16). The far right (120 sec.) mark indicates seizure onset. Other marks indicate 20 sec. increments prior to seizure onset, up to 2 minutes prior to the ictal event. These plots illustrate both agreement and synergy of the features at times 40, 60, and 110 secs., corresponding to 80, 60 and 10 sec. prior to seizure onset, respectively. The wavelet transform and spectrogram present greater lower frequency densities (dark shaded areas) at these times, which correlate with a peak in the parameterized measure of energy (FIG. 15). Similarly, a positive energy peak and a negative entropy peak (FIG. 16) correlate well as late precursors to seizure onset. Combinations of these and other features described above may also prove useful.

FIG. 17 is a plot of the fourth power indicator versus time, obtained by raising the energy signal amplitude to the fourth power. This plot more clearly demonstrates the bursts of power in the signal leading up to the ictal event that are not otherwise present at baseline.

FIG. 18 illustrates the plot of signal energy versus time for two separate one hour segments in a channel of first visible seizure onset. The top plot is for one hour prior to a patient's seizure. The bottom plot is taken approximately 8 hours away from any seizure activity. These plots indicate that the energy appears to fluctuate more prior to the seizure, frequency exceeding some limit in the hour prior to the seizure as opposed to other times distant from seizure activity. Thus, these changes may be detected as predictive of seizure onset in as much as one hour prior to seizure.

Of the features examined for the two-minute horizon, an interesting feature is the Pisarenko harmonic decomposition, which mathematically is represented or described by a fifth order polynomial of the form:

$$A(z^{-j}) = \Sigma z^{-1},$$

where $z^{-1}$ is a delay operator.

The roots of this polynomial lie on the unit circle in the complex plane. The impulse response of this model is a sum of sinusoids which provides a clean extraction of the alpha rhythm in the EEG signals.

Figure 19:
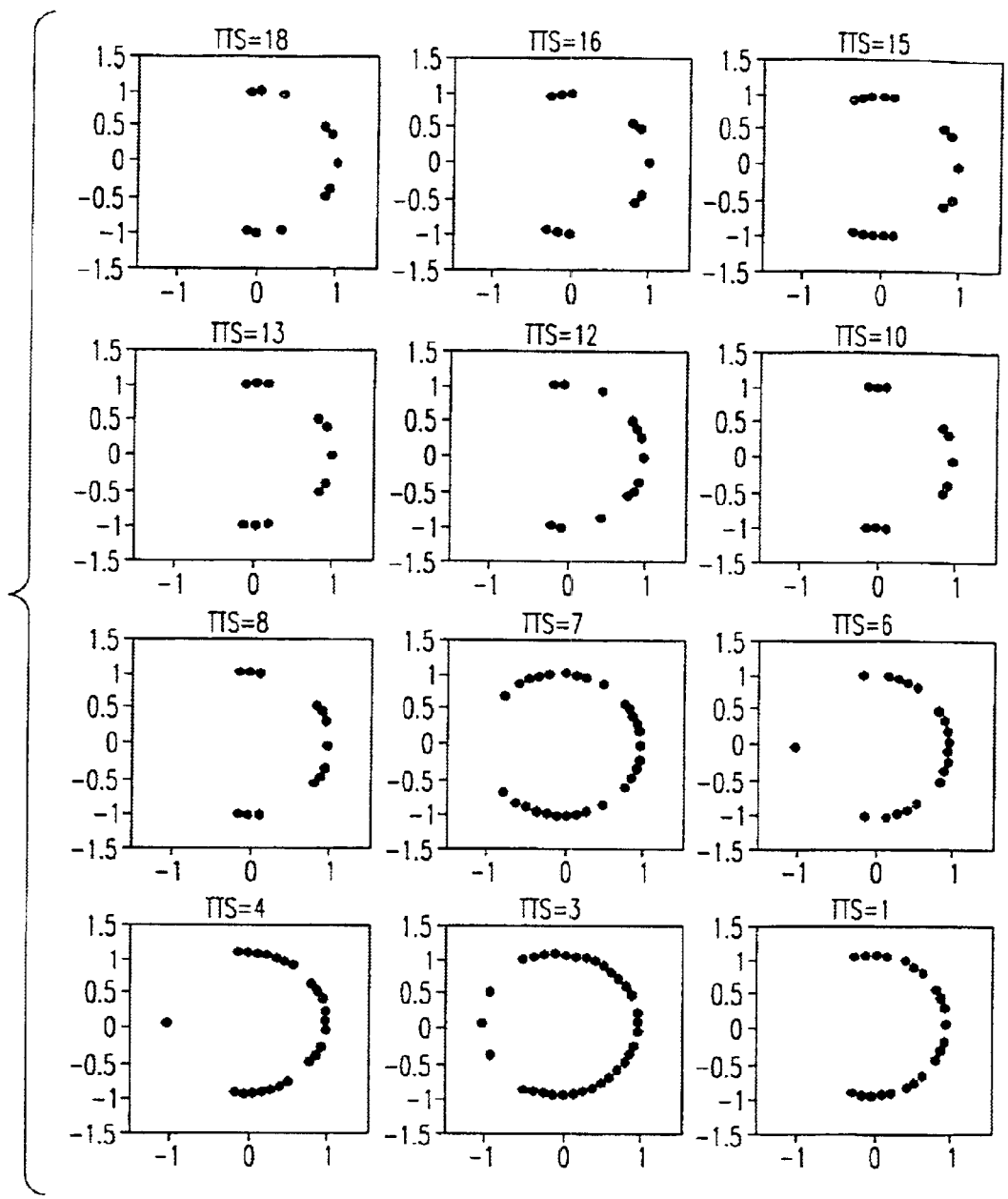
FIG. 19 illustrates several time frames of the complex root of a Pisarenko related feature preceding a seizure.

FIG. 19 illustrates the movement of the roots of the model polynomial in the complex plane at different instants of time leading up to seizure onset. In each plot, the horizontal axis is the real part of the root and the vertical axis is the imaginary part. There are fixed complex roots for each 256-point window. The window is moved one sample at a time through the signal for 300 window shifts before each plot is drawn. Each plot shown in FIG. 19 shows the poles every 5 samples, where "TTS" means time to seizure.

Of notable significance, for the entire two minutes preceding the seizure, the roots reside in very localized points along the unit circle in the same location as shown in the first seven frames in FIG. 19, then suddenly the roots begin to spread around the unit circle at approximately 60 seconds prior to seizure. This occurred for both seizures recorded from the same patient. These findings were not seen in homologous, contralateral channels. These results suggest reproducibility in 3 seizures tested, 2 from the same patient, and another from a second patient.

Figure 20:
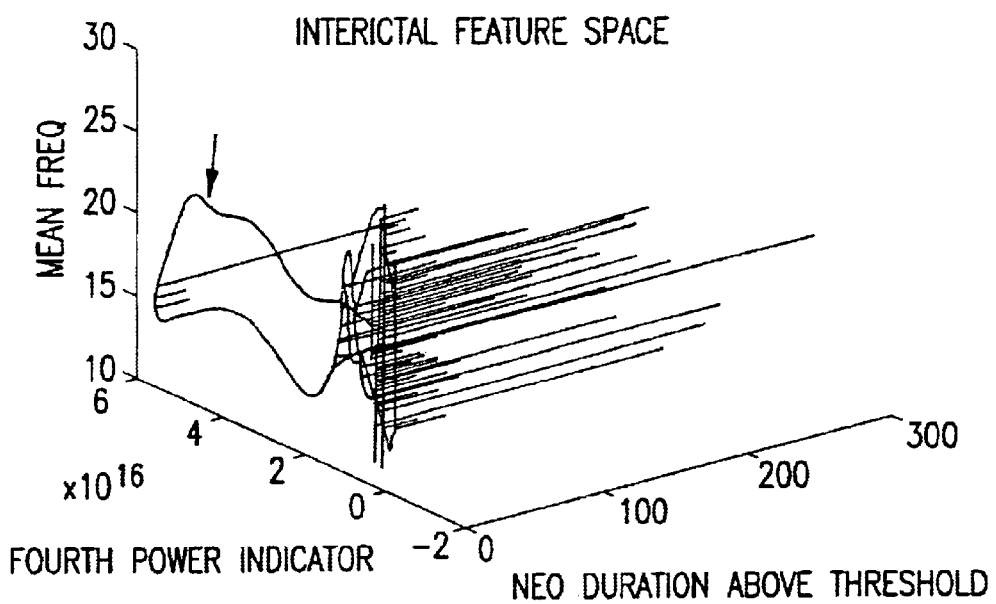
FIGS. 20–22 are graphical diagrams showing the trajectory of a three features in a three-dimensional feature space during interictal, pre-ictal and ictal periods of a patient having mesial temporal lobe epilepsy.
Figure 21:
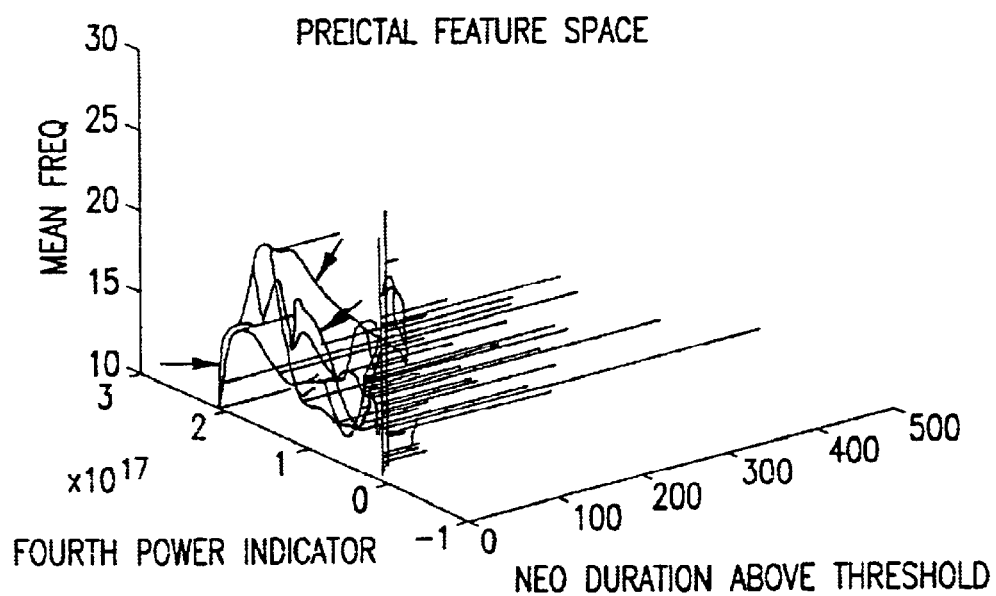
Figure 22:
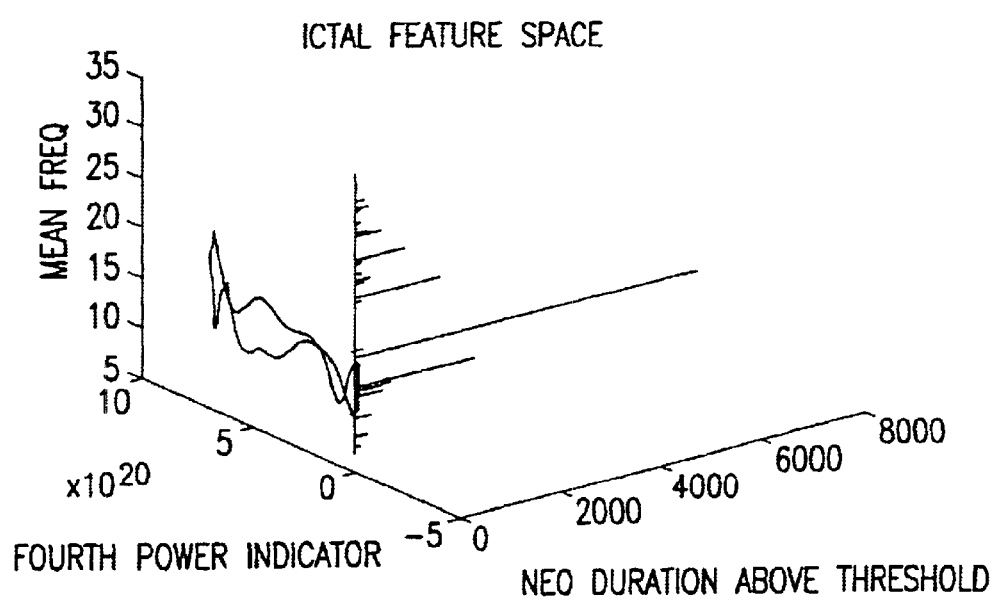

Referring now to FIGS. 20, 21 and 22, the changes in the trajectory of three features in a three-dimensional feature space are shown for interictal, pre-ictal and ictal states. The feature space consists of three features: (1) the mean frequency; (2) the fourth power indicator; and (3) the non-linear energy operator (NEO) duration above a threshold which is set to discriminate interictal, pre-ictal and ictal periods. The threshold for the NEO duration may be set arbitrarily or adaptively.

The data shown in these figures were derived from a 10-minute period of a single channel from a human depth electrode recording prior to and during a complex partial seizure of a human patient having mesial temporal lobe epilepsy. These figures demonstrate the synergy of these three features in distinguishing interictal, pre-ictal and ictal states, which is useful in predicting, and if necessary, detecting the onset of a seizure.

FIG. 20 shows that for most of the interictal period, the combined feature trajectory is confined to a narrow power band, with frequency fluctuation and NEO duration over broad ranges. One brief period demonstrates an "escape trajectory" indicated by the arrow in the figure representing a change from baseline conditions. This brief escape from baseline may represent an "attempt" to generate a seizure under conditions not otherwise conducive to seizure generation and propagation. Note that the fourth power indicator scale is $1 \times 10^{16}$.

FIG. 21 shows the feature trajectory during a pre-ictal period. Note that the fourth power indicator scale is $1 \times 10^{17}$. The feature trajectory in this figure demonstrates three consecutive "escapes" of increasing magnitude over time, indicated by the arrows, which herald the ictal state. In real-time viewing, these escape trajectories convey a progressive instability leading up to the ictal or seizure state. Escape trajectories begin several minutes prior to electrographic seizure onset.

FIG. 22 illustrates the feature trajectory during the ictal state. The fourth power indicator scale is $1 \times 10^{20}$. The seizure begins with a large "escape loop" followed by a global reduction in energy in the immediate post-ictal period.

Another promising feature for predicting epileptic seizures 20 to 50 minutes prior to EEG onset is accumulated energy. Accumulated energy (AE) was calculated in the region of seizure onset for 13 pre-seizure and 24 baseline recordings obtained from intracranial EEG (IEEG) recordings in 3 patients with mesial temporal lobe epilepsy (MTLE) during evaluation for epilepsy surgery. In all patients, pre-seizure AE deviated in a statistically significant fashion from trajectories calculated during periods far removed from seizure. Patterns of deviation differed between sleep and awake states in all patients. Our results indicate that AE is a useful feature for predicting seizure in patients with MTLE, and may complement other features for seizure prediction with different time horizons.

Figure 23:
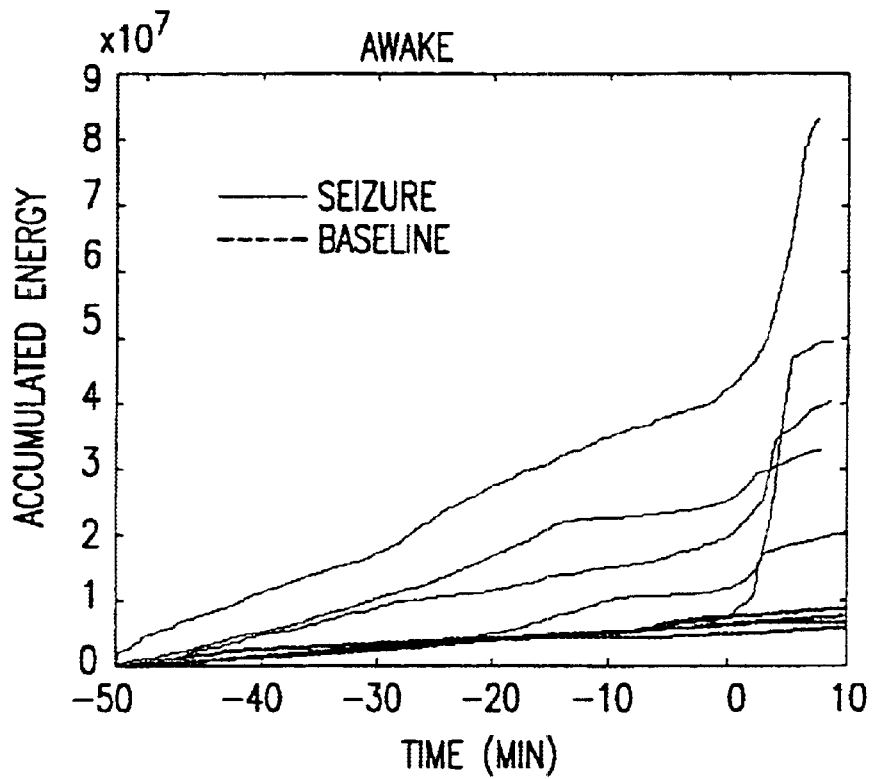
FIG. 23 is a graphical diagram illustrating accumulated energy for pre-seizure intervals and baseline intervals for an awake patient.
Figure 24:
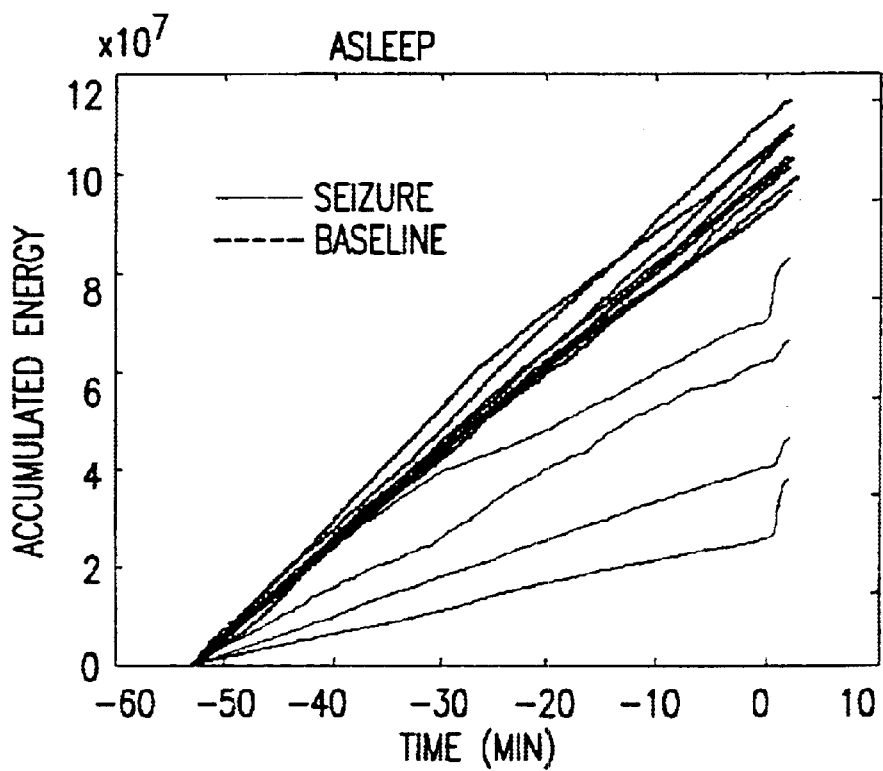
FIG. 24 is a graphical diagram illustrating accumulated energy for pre-seizure intervals and baseline intervals for an asleep patient.

Turning to FIGS. 23 and 24, accumulated energy as an important feature in seizure prediction will be described. The experimental setting underlying the data shown in FIGS. 23 and 24 is as follows. IEEG data were collected on a Nicolet 5000 Video-EEG acquisition unit. Data were digitally sampled at 200 Hz. Bipolar signals were derived from intracranial depth and strip electrodes to eliminate common mode artifacts, then 60 Hz notch filtering was performed to eliminate line noise. Thirteen pre-seizure and 24 randomly chosen baseline ($\geq 8$ hrs from seizure) 50–60 minute IEEG segments were analyzed. Sleep/wake cycles were derived from EEG and patient video data. The AE feature was extracted from the energy of the measured IEEG time series, as explained above.

Of the 13 pre-seizure and 24 baseline intervals analyzed, all but 1 pre-seizure and 1 baseline trajectory were linearly separable within patients. FIG. 23 presents AE plotted for 5 pre-seizure and 4 baseline intervals for patient 1. Four of five pre-seizure intervals demonstrate trajectories that deviate significantly from the baseline recordings 20 or more minutes prior to seizure onset. One pre-seizure interval continues on a "baseline trajectory" until seizure onset. FIG. 24 shows AE plotted for 4 pre-seizure and 9 baseline intervals during sleep for patient 2. Again, pre-seizure AE trajectories significantly deviated from baseline AE 20 to 50 minutes prior to seizure onset.

Figure 25:
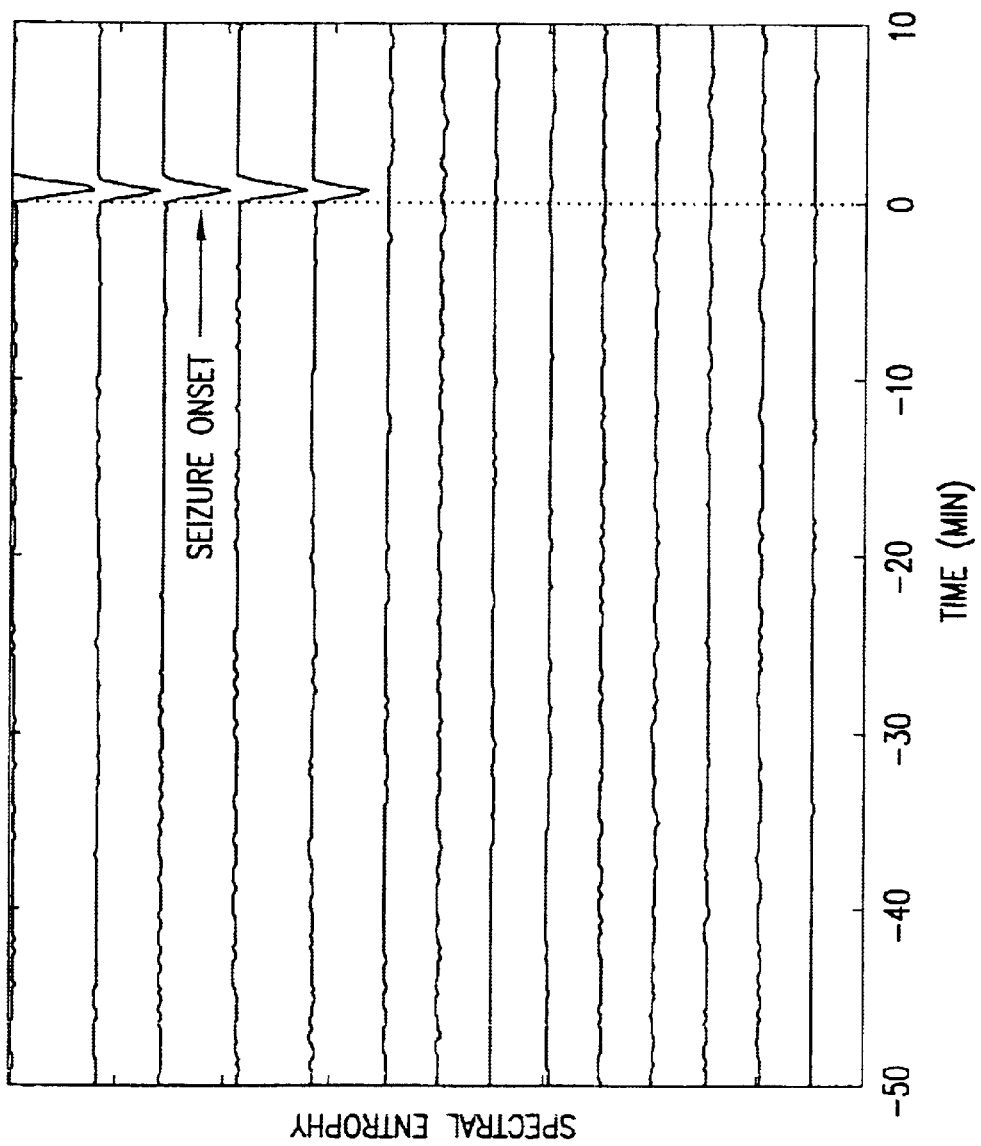
FIG. 25 is a graphical diagram illustrating spectral entropy for five pre-seizure intervals and nine baseline intervals for a patient.

With reference to FIG. 25, still another feature is spectral entropy (SE). FIG. 25 shows SE for five pre-seizure intervals and nine baseline intervals for a patient. The down slope on the top five tracings coincides with seizure onset.

The spectral entropies of intracranial EEG signals were recorded from six patients with mesial temporal lobe epilepsy. Sixty minute segments of 35 pre-seizure and 50 randomly chosen baselines (6 hours from the seizure) were analyzed from a total of 6 patients by evaluating bipolar channels in the ictal onset zone, derived from digital IEEG signals recorded referentially. Spectral entropies were calculated in a sliding window of 30 seconds with 50% overlap.

Significant changes in SE were observed in all of the 6 patients evaluated. The SE successfully detected the unequivocal electrographic onset (UEO) in all 6 patients and predicted 17 of the 25 seizures in 4 of the patients over a range of 1 to 20 seconds prior to UEO. A decrease in SE occurred on or before the UEO indicating increased organization of activity prior to and during a seizure.

SE provides a measure of organization in neural function which preliminary experiments suggest may be useful in seizure prediction and detection. In the setting of MTLE, SE may detect synchronization of activity in the ictal onset and epileptogenic zones which may be indicative of imminent seizure onset and propagation. Spectral entropy is among a number of promising quantitative features which may synergistically forecast seizures and help determine a mechanism for ictogenesis in MTLE.

Figure 26:
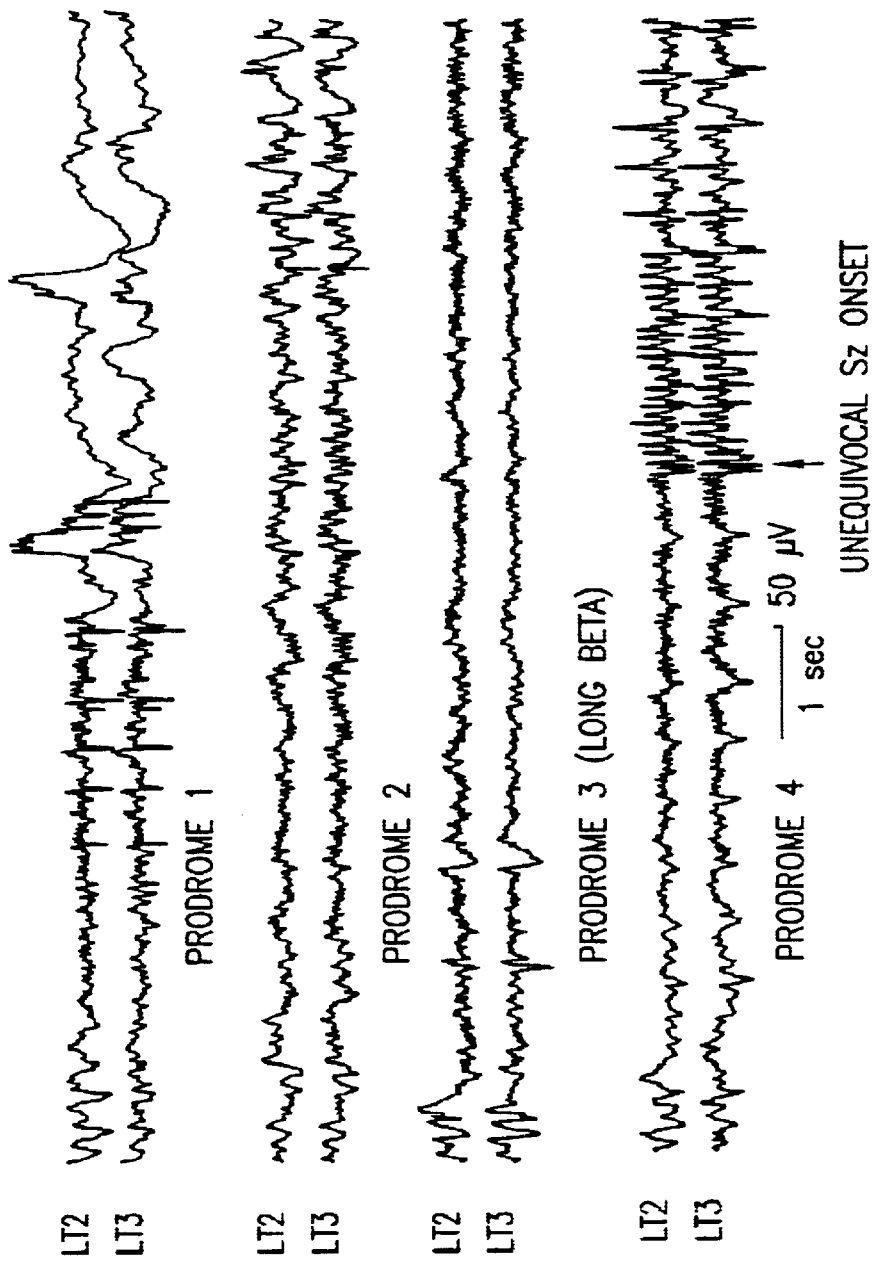
FIG. 26 shows graphical diagrams illustrating four types of high frequency rhythmic prodromes, one of which gives rise to a seizure.

Turning to FIGS. 26–29, the utility of prodromes will be described. Pre-ictal Prodromes are specific pre-ictal patterns which occur on the EEG, either visible to the eye or only discovered computationally, which herald seizure onset. They may increase in their frequency of occurrence, their amplitude or their duration as the seizure approaches. FIG. 26 illustrates one example of a prodrome, visible to the eye as high frequency rhythmic activity which "evolves" in frequency and amplitude over time. Four prodromes are shown in FIG. 26. The first three are self-limited and dissipate. The fourth prodrome gives rise to a seizure.

Figure 27:
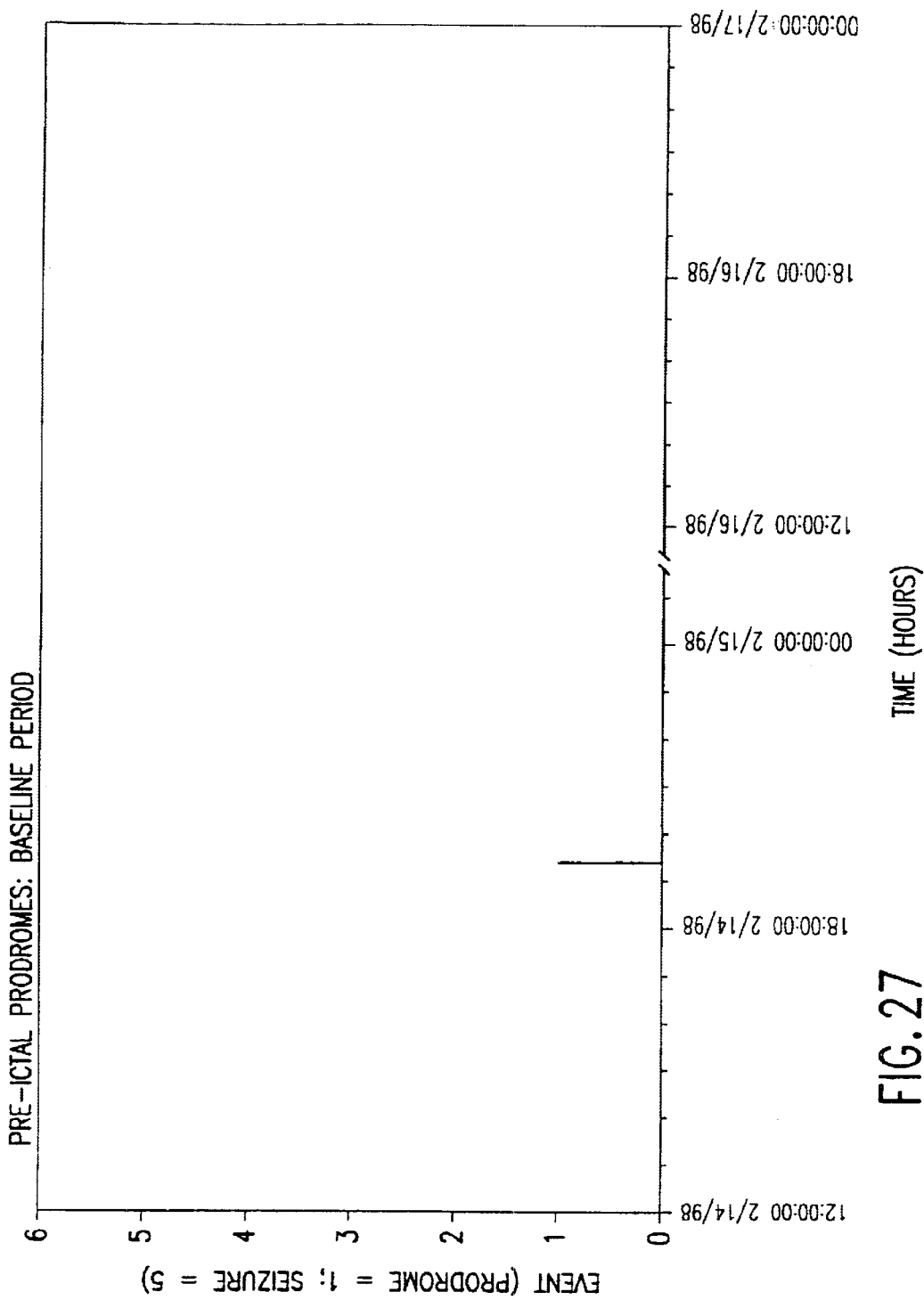
FIG. 27 is a graphical diagram showing that pre-ictal prodromes are rare at times far removed from seizure onset

FIG. 27 demonstrates that this particular prodrome is rare and far removed from seizures, i.e., it occurs one time. In particular, this diagram shows the occurrence of the pre-ictal prodromes during a 26 hour baseline period, far removed from any seizures.

Figure 28:
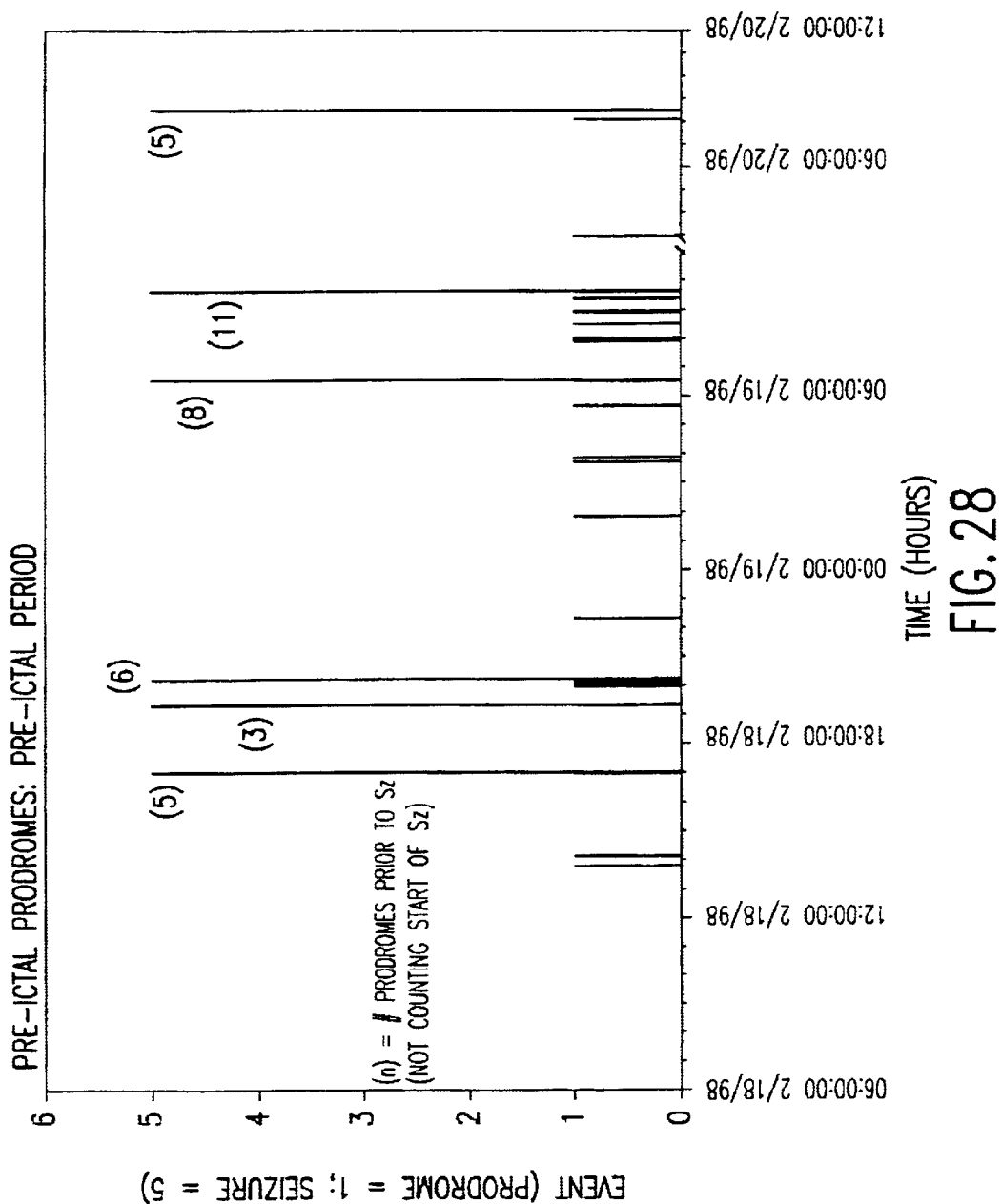
FIG. 28 is a graphical diagram showing the activity of pre-ictal prodromes increases as a seizure approaches.

FIG. 28 demonstrates that the occurrence of this activity increases as seizures approach. In particular, this figure shows the occurrence of pre-ictal prodromes prior to seizure onset during a 38 hour period surrounding seizures. The numbers in parentheses indicate the number of prodromes detected prior to seizure onset, not including the "terminal" prodrome which actually begins the seizure. Since prodromes cluster near the time of seizure onset, they are not all easily seen, and the number of prodromes prior to each seizure is written in parentheses next to each seizure line on the graph. In summary, this FIG. 28 shows that pre-ictal prodromes occur almost exclusively within 3 hours of seizure onset, and are predictive of oncoming seizures. They often cluster together prior to seizure onset. The lines of amplitude=1 are pre-ictal prodromes. Thick lines demonstrate clusters of prodromes-prior to seizures. Lines of amplitude=5 are seizures (6 in total). The numbers in parentheses represent the number of times these prodromes occurred prior to each seizure.

Figure 29:
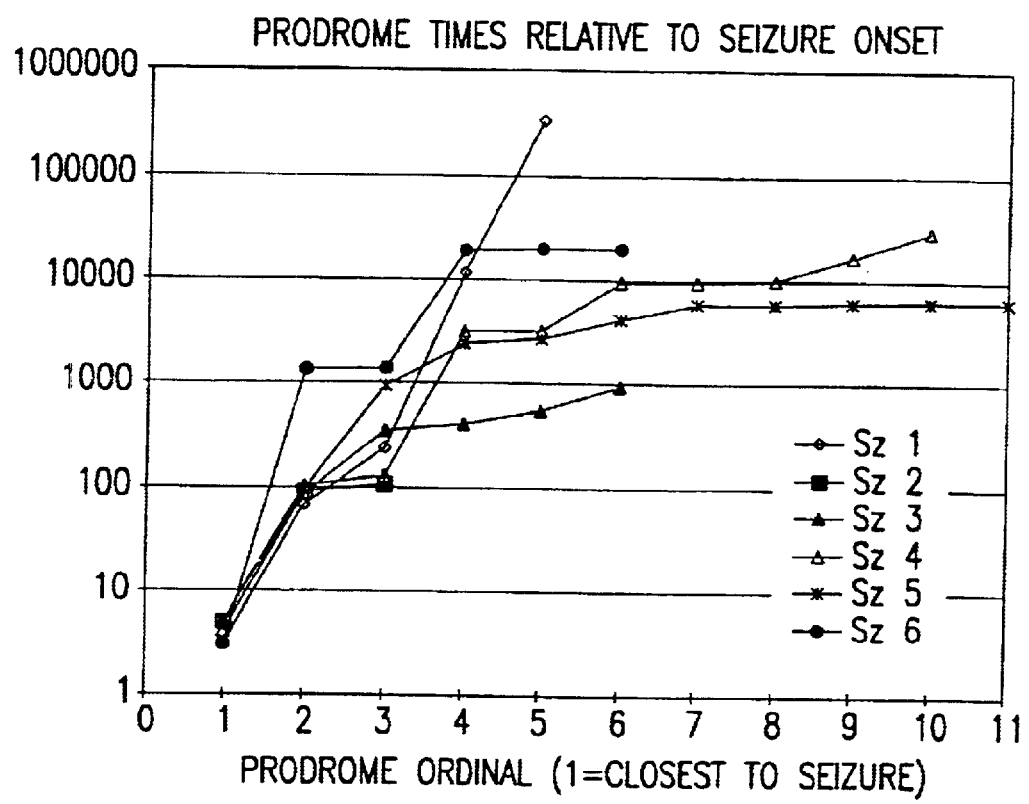
FIG. 29 is a graphical diagram that shows the occurrence of pre-ictal prodromes in a single patient prior to six different seizures.

FIG. 29 depicts the predictive horizon of the prodromes for the same patient as in FIGS. 26–28, and their time of occurrence relative to seizure onset. The prodromes occurring at the #1 position occur closest to seizure onset. Seizures have a variable number of pre-ictal prodromes ranging up to 11 per seizure onset. In this patient, most prodromes began on average of 2.5 to 3 hours prior to seizure onset. This figure demonstrates that in most cases pre-ictal prodromes occur within 3 hours of unequivocal electrical seizure onset. In this scheme, it is evident that the majority of the prodromes occur between 10,000 and 15,000 seconds before seizure onset. A stepped treatment scheme, escalating in strength of treatment, can be tied to prodrome detection, which can be either quantitative, feature driven, or accomplished via pattern matching. A mild intervention might be triggered with detection of a single prodrome. This intervention is escalated with detection of further prodromes, as a function of their number, the period of time elapsed between them, and characteristics of the prodromes themselves, such as their amplitude, duration, and frequency characteristics.

A specific example of this system is as follows. A feature vector for a particular patient is generated that contains windowed (i.e. calculated over a particular time window, such as 1.25 seconds) features such as mean frequency, 4th power indicator, a single scale of the wavelet transform; spectral entropy, and signal energy. A complementary historical feature vector is generated that contain counts of the occurrence of a pre-ictal prodrome in the last "n" time windows (by template matching or frequency/time domain characteristics), counts of drops in fractal dimension for the last "n" windows below a certain threshold, and features of accumulated energy profiles including the last value and number of slope changes. Both of these feature vectors are fed into the series of wavelet neural networks and probabilities of seizure occurrence for each time horizon are continuously calculated. Higher actual probabilities occur when several pre-ictal prodromes are detected in a 3 hour period, when the trend in accumulated energy deviates by a certain threshold amount from baseline tracings, or when the WNNs calculate increased probability of a seizure based on feature behavior that is not generally visible to the naked eye.

In summary, the present invention is directed to a fully automatic implantable system (apparatus and method) for monitoring electrical activity of the brain, extracting a set of (at least one) features from the measured brain activity determined, a priori, to be predictive of seizure onset (in a particular individual, a class of individuals or all individuals), continuously analyzing the set of features derived from real-time brain activity data and other complementary physiologic parameters with an intelligent prediction subsystem trained to predict when a seizure in the brain is imminent based on the set of features, and generating an output indicative of the likelihood of seizure occurrence. The method may further include the step of automatically alerting a patient and/or delivering intervention measures (pharmacologically, electrical, etc.) to abort or modulate the seizure. The patient may set predetermined thresholds of probability measures to control when alerts are generated and/or when preventative action is taken. In addition, if seizure prediction is missed, the system will detect the seizure and appropriate action can be taken by the patient in response to a system alert.

The present invention involves a self-learning intelligence structure which will download data periodically and improve its own performance over time. Some of the processing, training and learning may take place off-line on a PC (desktop or portable) at a visiting office unit or via the Internet, cellular telephone network, or other communication medium.

Other features and advantages of the present invention that are new are:

1. Bias adjustment of the outputs to reflect the relatively low probability of seizure occurrence over time in most individuals, which has the effect of lowering false alarm rates.
2. Artificially creating optimized features for use in conjunction with conventional features as inputs into the probability estimation structure (i.e., the predictor). These features may be synthesized by the trainable intelligent structure of the system as it learns.

The system and method according to the present invention provide several unique features and advantages over known technologies. For example, the present invention employs continuous probabilistic forecasting, and continuously outputs a probability measure, which is an estimation of the exact probability function determined for seizure occurrence according to the prediction methods of the present invention. In addition, the present invention employs multiple adjustable prediction time periods or time frames. Also unique to this invention, therapeutic intervention triggered by this prediction method is adjusted according to the probability measure output and/or time horizon to seizure so that as seizures become closer and more likely, modalities or parameters of the intervention measure (duration, strength, etc.), such as a more aggressive therapy, is triggered to abort the event.

Continuous probability outputs have advantages such as providing empirical degrees of confidence, easy conversion into on-off warning signals, and use as a continuous control for automatic drug delivery or seizure-mitigating electrical measures. That is, a character of a seizure treatment or intervention measure (such as strength, duration, intensity, etc.) can be based on the continuous probability output, its integral, derivative, and/or any of its mathematical function (linear or nonlinear) thereof.

Accordingly, another aspect of the present invention, which has utility independent of the method of predicting onset of seizures and estimating the probability seizure onset, involves applying intervention measures to an animal to abort or modulate a seizure comprising by adjusting the modality of an intervention measure and/or parameters of an intervention measure based upon a probability measure indicative of a likelihood of seizure occurrence and/or a predicted time to seizure onset. These methods control the interaction between diagnostic and therapeutic portions of seizure prediction and treatment system. A variety (i.e., modalities) of intervention measures are applied to abort or modulate a seizure, such as:

1. electrical stimulation to abort a seizure
2. pacing paradigms or patterns of electrical stimulation
3. local infusion of drugs or chemicals such as benzodiazepines, antiepileptic drugs, neurotransmitters or their agnonists and antagonists, behavioral stimuli, the duration and/or intensity of which is related to a particular neural signal to cancel patterns known to precede or induce seizures.

For example, the modalities of intervention measures (and parameters thereof) may track algorithms which predict EEG and/or clinical onset of seizures based upon multiple features of a feature set, such as the EEG and/or a variety of other physiological parameters including electrocardiogram and other features derived from it (e.g. heart rate variability), pupillary diameter, skin resistance, respiratory rate, serum catecholamines.

In this scheme, a monitoring algorithm looks for information in the biological parameters modeled that signal seizure onset or an approaching seizure. Based upon previously selected threshold criteria, such as a relatively low probability measure and/or relatively remote time to seizure onset (prediction horizon), a particular modality and character or parameters of treatment or intervention measure is chosen for an initial treatment response. If the initial treatment response is ineffective, and/or seizure indicators continue to indicate an approaching seizure (e.g. increasing probability of seizure occurrence and/or less remote time to seizure onset), subsequent treatment responses are escalated, either by escalating a character or parameters of an intervention measure, changing modalities, or a combination of both may be chosen (possibly in turn or in combination with initial treatment responses) in a "stronger" attempt to arrest the development of seizures. For example, initial therapy might be a mild pacing current in the region of seizure onset. Should this fail after a particular time period, such as 10 seconds, the current level of the pacing signals may then be escalated and/or the frequency of stimulation altered in an attempt to have more efficacy. Should this again fail, a local infusion of a small amount of a chemical agent or drug to abort seizures may be triggered. Should this still fail, further, more aggressive treatment, potentially including other treatment modalities may be initiated. Finally, if electrical and or clinical seizure onset are detected, maximal intensity treatment with a variety of modalities (pacing, electrical shock, drugs, etc.) may be administered in an attempt to minimized clinical effect from the seizure.

Additionally, these intervention measures may be arranged so that the milder therapies, with fewest side effects are administered/are triggered in response to programmed alarms or thresholds with high sensitivity and lower selectivity, as a higher false positive rate may be well tolerated in this scenario; that is, treatments with few side effects administered far in time from a seizure. As more aggressive therapy may be required, as a seizure becomes more imminent, other alarm thresholds may be employed which have a much higher specificity, as tolerance for false positive and negative alarms may be less well tolerated when triggering therapeutic responses with greater clinical effects and greater side effects. Finally, after seizure onset, as detected by a highly sensitive and selective algorithm, a maximal "seizure-arresting" responsive intervention measure may be triggered.

Some of the activities that are monitored and used for determining therapeutic response may be specific EEG patterns, such as increasing complexity of interictal epileptiform discharges, increasing disruption of background activity and/or specific patterns heralding higher probability of seizure onset, such as pre-ictal prodromes.

In addition, the present invention is directed to a method for predicting the probability of seizure onset from electrochemical measures of brain activity, based upon detection and categorization of a cascade of neurophysiologic changes in the brain which occur over time (from days, hours, minutes and seconds) prior to and at seizure onset, known to lead to clinically significant epileptic seizures.

The methods for predicting seizure onset and for controlling the application of intervention measures may be implemented entirely through software programs(s) executed by a processor on a variety of hardware platforms. In this regard, it is to be understood that these software programs may be embodied as a processor readable memory medium storing instructions, which when executed by a processor, perform the various prediction and related intervention control steps described above.

The above description is intended by way of example only and is not intended to limit the present invention in any way except as set forth in the following claims.

What is claimed is:

1. A method for automatically predicting the onset of a seizure in an animal, comprising steps of:
   (a) monitoring signals indicative of the activity of the brain of an animal;
   (b) extracting a set of features from the signals;
   (c) analyzing the set of features with a intelligent prediction subsystem; and
   (d) generating, in response to analysis of the set of features by the intelligent prediction subsystem, an output indicative of the probability of occurrence of a seizure.

2. The method of claim 1, wherein the step of generating an output comprises generating a warning that a seizure is likely to occur.

3. The method of claim 1, wherein the step of generating an output comprises generating a measure of probability that a seizure will occur within a pre-identified time period.

4. The method of claim 3, and further comprising the steps of:
   setting a probability threshold;
   monitoring the probability and comparing it with the probability threshold; and
   issuing an audible and/or visual warning alert when the probability exceeds the probability threshold.

5. The method of claim 3, wherein the step of generating an output comprises generating a plurality of probability measures each for a different time period.

6. The method of claim 5, and further comprising the step of applying an intervention measure, a character of which is based the probability measure and/or a predicted time to seizure occurrence.

7. The method of claim 1, and further comprising the step of applying an intervention measure beginning with an initial response when triggered in response to a relatively low probability measure and/or relatively remote predicted time to seizure onset, and escalating a character and/or modality of the intervention measure as the probability measure increases and/or predicted time to seizure onset is less remote.

8. The method of claim 7, wherein the step of applying an intervention measure comprises applying an intervention measure at a maximal intensity and/or combination of modalities when a feature identifies electrographic seizure onset.

9. The method of claim 1, and further comprising the step of applying intervention measures comprising pharmacological, cardiac pacing and/or electrical preventative measures to the animal when a seizure is predicted in order to terminate a seizure prior to its electrical or clinical onset, or to terminate a seizure after onset.

10. The method of claim 1, wherein the step (b) of extracting the set of features comprises extracting one or more instantaneous features.

11. The method of claim 1, wherein the step (b) of extracting the set of features comprises extracting one or more historical features.

12. The method of claim 11, wherein the step (b) of extracting the set of features comprises extracting one or more historical features using statistical process control techniques.

13. The method of claim 1, wherein the step (b) of extracting the set of features comprises artificially generating one or more features from the signals.

14. The method of claim 1, and further comprising the step of training the intelligent prediction subsystem to predict the onset of a seizure prior to its occurrence for a particular animal from data including signals indicative of the activity of the brain of a particular animal.

15. The method of claim 14, and further comprising the step of storing the data including signals indicative of the activity of the brain of a particular animal prior to and during a seizure event of the particular animal.

16. The method of claim 1, wherein the step (a) of monitoring signals comprises monitoring brain activity signals and other physiological signals indicative of the brain activity.

17. The method of claim 1, wherein the step of generating an output comprises generating a continuously updated probability measure indicative of the likelihood of occurrence of a seizure.

18. The method of claim 17, wherein the step of generating the probability measure comprises estimating the exact conditional probability function.

19. The method of claim 17, and further comprising the step of applying an intervention measure, a character of which is based on a mathematical function of the probability measure.

20. A method for automatically predicting the onset of a seizure in an animal, comprising steps of:
(a) monitoring signals indicative of the activity of the brain of an animal;
(b) extracting a set of features from the signals;
(c) forming a feature vector that is a combination of a plurality of features extracted from the signals;
(d) analyzing the set of features with a intelligent prediction subsystem; and
(e) generating an output indicative of the likelihood of occurrence of a seizure.

21. A system for predicting the onset of a seizure in an animal, comprising:
(a) at least one electrode for detecting signals indicative of the activity of the brain of animal;
(b) a processor coupled to the at least one electrode, the processor:
extracting a set of features from the brain activity signals;
forming a feature vector that is a combination of a plurality of features extracted from the signals;
continuously analyzing the set of features with a intelligent prediction process; and
generating as output a signal indicative of the likelihood of occurrence of a seizure.

22. A system for predicting the onset of a seizure in an animal, comprising:
(a) at least one electrode for detecting signals indicative of the activity of the brain of animal;
(b) a processor coupled to the at least one electrode, the processor:
extracting a set of features from the brain activity signals;
continuously analyzing the set of features with a intelligent prediction process; and
generating as output, in response to continuous analysis of the set of features by the intelligent prediction process, a signal indicative of the probability of occurrence of a seizure.

23. The system of claim 22, wherein a predictor algorithm to be executed by the processor is trained "off-line" with data comprising signals indicative of brain activity obtained from a particular animal so as to operate "on-line" in real-time on signals obtained by the at least one electrode coupled to the particular individual.

24. The system of claim 22, wherein the processor is contained with an implantable unit for implantation in a body of an animal.

25. The system of claim 24, and further comprising a portable unit external of the body of the animal that communicates with the implantable unit via a communication link through the body of the animal, the portable unit comprising an alert device, the processor in the implantable unit generating as output a signal that activates the alert device in response to determining onset of a seizure.

26. The system of claim 25, wherein the portable unit comprises a display, wherein the processor generates a warning message that is transmitted via the communication link to the display.

27. The system of claim 25, wherein information stored in the implanted unit is uploaded through the portable unit for transmission to an external computer via a communications network or the Internet.

28. The system of claim 21, wherein the processor generates an output comprising a probability measure representing the probability that a seizure will occur within a period of time.

29. The system of claim 28, wherein the processor generates as output a plurality of probability measures, each for a different time period.

30. The system of claim 29, wherein the processor generates a signal to cause application of an intervention measure, a character of which is based on the probability measure.

31. The system of claim 21, wherein the processor implements a trainable intelligence network as the intelligent prediction subsystem to analyze the set of features.

32. The system of claim 31, wherein the processor implements the intelligent prediction process with a wavelet neural network (WNN).

33. The system of claim 21, wherein the processor detects seizure onset from the set of features and generates a signal for causing the delivery of an intervention measure whose character is based upon multiple features of the feature set.

34. A method of automatically predicting the onset of a seizure comprising steps of:

(a) extracting a plurality of features from signals indicative of the brain activity of an animal;

(b) examining the plurality of features and selecting a subset of the plurality of features determined to predictive of seizure onset in the individual;

(c) training a intelligent prediction subsystem to predict a seizure in the individual based on the subset of features;

(d) continuously extracting the subset of features from real-time brain activity signals of an individual;

(e) continuously analyzing the subset of features with the intelligent prediction subsystem; and (f) continuously generating as output a probability measure that a seizure will occur within a predetermined period of time.

35. The method of claim 34, wherein the step (f) of continuously generating comprises generating a plurality of probability measures each with respect to a different prediction time horizon.

36. The method of claim 34, wherein the step (c) of training comprises periodically training the intelligent prediction subsystem based on seizure and baseline data extracted for a particular animal to maintain performance of the intelligent prediction subsystem independent of conditions of the particular animal.

37. A method for applying intervention measures to an animal to abort or modulate a seizure comprising the step of adjusting the modality of an intervention measure and/or parameters of an intervention measure based upon a probability measure indicative of a likelihood of seizure occurrence and/or a predicted time to seizure onset.

38. The method of claim 37, wherein the step of adjusting comprises applying an intervention measure beginning with an initial response when triggered in response to a relatively low probability measure and/or relatively remote time to seizure onset, and escalating a character and/or modality of the intervention measure as the probability measure increases and/or time to seizure onset is less remote.

39. The method of claim 38, wherein the step of applying an intervention measure comprises applying an intervention measure at a maximal intensity and/or combination of modalities when a feature identifies electrographic seizure onset.

* * * * *